(12) United States Patent
Bennett et al.

(10) Patent No.: US 8,965,516 B2
(45) Date of Patent: Feb. 24, 2015

(54) SYSTEM AND METHOD FOR TREATMENT OF PAIN RELATED TO LIMB JOINT REPLACEMENT SURGERY

(71) Applicant: SPR Therapeutics, LLC, Cleveland, OH (US)

(72) Inventors: Maria E. Bennett, Beachwood, OH (US); Joseph W. Boggs, Carrboro, NC (US); Amorn Wongsarnpigoon, Morrisville, NC (US); John Chae, Strongsville, OH (US); Warren P. Grill, Chapel Hill, NC (US); Kathryn Stager, University Heights, OH (US); Rosemary Zang, Avon Lake, OH (US)

(73) Assignee: SPR Therapeutics, LLC, Cleveland, OH (US)

( * ) Notice: Subject to any disclaimer, the term of this patent is extended or adjusted under 35 U.S.C. 154(b) by 0 days.

(21) Appl. No.: 13/791,710

(22) Filed: Mar. 8, 2013

(65) Prior Publication Data
US 2013/0253605 A1 Sep. 26, 2013

Related U.S. Application Data

(60) Provisional application No. 61/608,106, filed on Mar. 8, 2012.

(51) Int. Cl.
A61N 1/05 (2006.01)
A61N 1/36 (2006.01)

(52) U.S. Cl.
CPC .......... *A61N 1/36071* (2013.01); *A61N 1/0502* (2013.01); *A61N 1/36017* (2013.01); *A61N 1/36021* (2013.01)
USPC ................................. 607/46; 607/2

(58) Field of Classification Search
CPC ..................... A61N 1/36021; A61N 1/36071
USPC ....................................... 607/2, 46
See application file for complete search history.

(56) References Cited

U.S. PATENT DOCUMENTS 6,845,271 B2   1/2005  Fang et al.
7,302,296 B1 * 11/2007 Hoffer ........................... 607/48

(Continued)

FOREIGN PATENT DOCUMENTS

WO    WO2005105201 A2    11/2005

OTHER PUBLICATIONS

U.S. Appl. No. 13/605,653, filed Sep. 6, 2012, Inventors: Joseph W. Boggs, II, et al.

(Continued)

*Primary Examiner* — Niketa Patel
*Assistant Examiner* — Christopher A Flory
(74) *Attorney, Agent, or Firm* — McDonald Hopkins LLC

(57) ABSTRACT

It has been discovered that pain felt in a given region of the body can be treated by stimulating a peripheral nerve at a therapeutically effective distance from the region where pain is felt to generate a comfortable sensation (i.e., paresthesia) overlapping the regions of pain. A method has been developed to reduce pain in a painful region following limb joint replacement by stimulating a peripheral nerve innervating the painful region with an electrode inserted into tissue and spaced from the peripheral nerve. This method may be used to help alleviate postoperative pain in patients following total knee arthroplasty surgery or other limb joint replacement surgeries.

20 Claims, 19 Drawing Sheets

(56) References Cited

U.S. PATENT DOCUMENTS

| | | |
|---|---|---|
| 8,249,713 B2 | 8/2012 | Fang et al. |
| 8,626,302 B2 * | 1/2014 | Bennett et al. .................. 607/46 |
| 8,644,941 B2 * | 2/2014 | Rooney et al. .................. 607/46 |
| 2003/0130706 A1 * | 7/2003 | Sheffield et al. ................ 607/46 |
| 2005/0105201 A1 | 5/2005 | Christie, Jr. et al. |
| 2007/0073356 A1 * | 3/2007 | Rooney et al. .................. 607/46 |
| 2007/0073357 A1 * | 3/2007 | Rooney et al. .................. 607/46 |
| 2007/0213771 A1 * | 9/2007 | Spinner et al. .................... 607/2 |
| 2009/0221928 A1 * | 9/2009 | Einav et al. .................... 600/544 |
| 2009/0281594 A1 * | 11/2009 | King et al. ...................... 607/46 |
| 2010/0036454 A1 | 2/2010 | Bennett et al. |
| 2010/0152808 A1 | 6/2010 | Boggs, II |
| 2010/0152809 A1 | 6/2010 | Boggs, II |
| 2011/0208266 A1 | 8/2011 | Minogue et al. |
| 2012/0232615 A1 * | 9/2012 | Barolat et al. .................. 607/46 |
| 2012/0290055 A1 | 11/2012 | Boggs, II |
| 2012/0310301 A1 | 12/2012 | Bennett et al. |
| 2012/0310302 A1 | 12/2012 | Bennett et al. |
| 2012/0310314 A1 | 12/2012 | Bennett et al. |
| 2013/0013041 A1 * | 1/2013 | Glukhovsky et al. ......... 607/116 |
| 2013/0066393 A1 * | 3/2013 | Gross et al. ..................... 607/46 |
| 2013/0096641 A1 | 4/2013 | Strother |
| 2013/0197615 A1 | 8/2013 | Rundle |
| 2013/0238066 A1 * | 9/2013 | Boggs et al. .................. 607/116 |
| 2013/0253605 A1 * | 9/2013 | Bennett et al. .................. 607/46 |
| 2014/0046416 A1 * | 2/2014 | Bennett et al. ................ 607/116 |

OTHER PUBLICATIONS

U.S. Appl. No. 13/843,002, filed Aug. 7, 2013, Inventors: Amorn Wongsarnpigoon, et al.

International Search Report and the Written Opinion of the International Searching Authority, SPR Therapeutics, LLC, May 31, 2013.

* cited by examiner

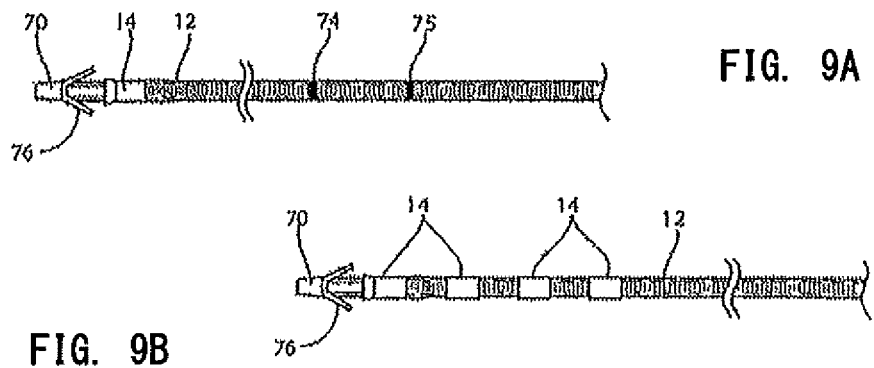

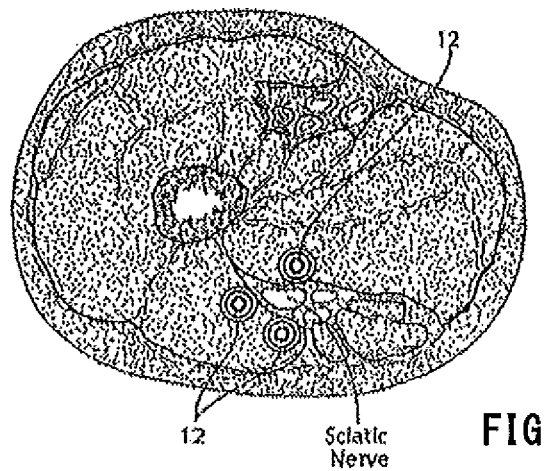
FIG. 13A
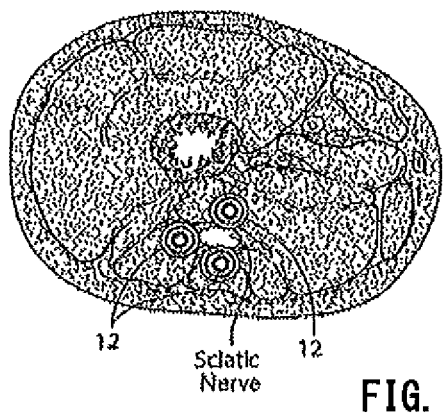 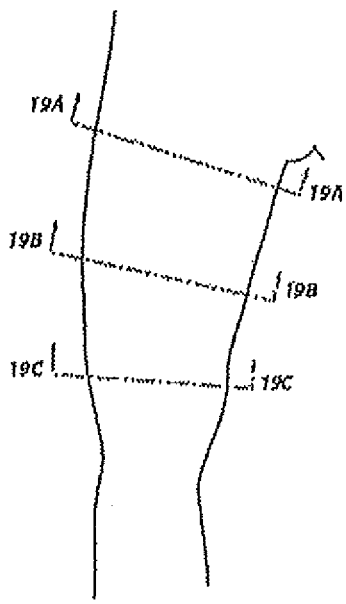
FIG. 13B
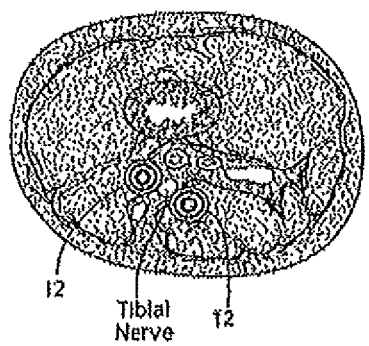
FIG. 13C

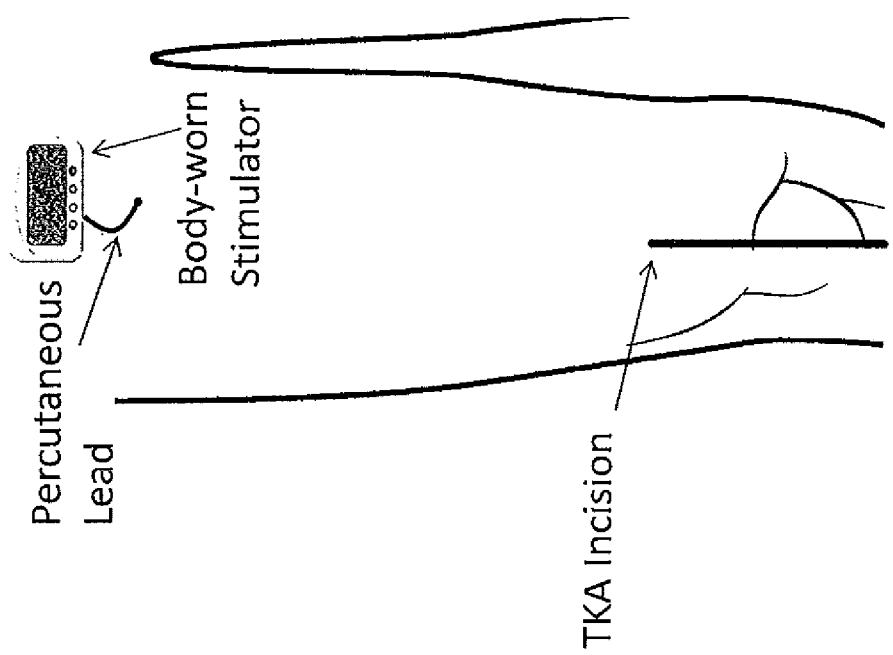

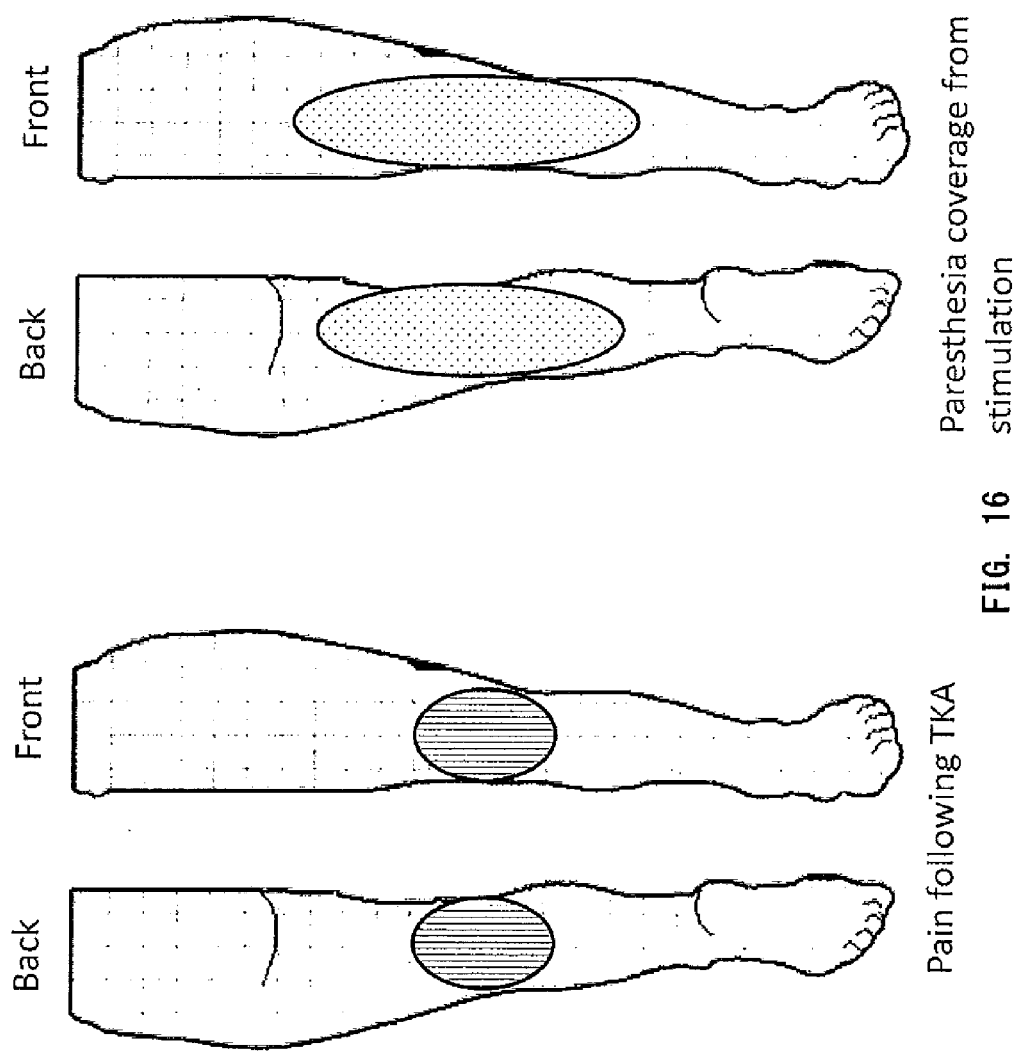

SYSTEM AND METHOD FOR TREATMENT OF PAIN RELATED TO LIMB JOINT REPLACEMENT SURGERY

CROSS-REFERENCE TO RELATED APPLICATION

This application claims the benefit from U.S. Provisional Patent Application No. 61/608,106 entitled "Systems and Methods for Bodily Conditioning and Treatment of Pain Related to Surgery" filed on Mar. 8, 2012, which is hereby incorporated in its entirety by reference.

FIELD OF INVENTION

The present invention generally relates to a system and a method to deliver electrical stimulation to treat post-operative pain following limb joint replacement surgery.

BACKGROUND OF THE INVENTION

Limb joint replacement surgery is often able to provide patients with a remarkable improvement in their health. However, these surgeries often require significant rehabilitation often eliminating it as a treatment alternative for patients. Moreover, the pain associated with these surgeries can cause a delay in rehabilitation potentially reducing the efficacy of such treatments. In order for patients to begin rehabilitation promptly to increase the likelihood of success of such surgeries, it is imperative that the pain following the limb joint replacement surgery be managed.

While existing systems and techniques can offer some relief and ancillary benefits to individuals requiring therapeutic relief, many issues and the need for improvements still remain. For example, non-narcotic analgesics, such as acetaminophen or non-steroidal anti-inflammatory drugs (NSAIDS), have relatively minor side effects and are commonly used for several types of pain. However, they are rarely sufficient in managing moderate to severe postoperative pain.

The use of narcotic analgesics, such as opioids, has shown only minor success with inconsistent results. Narcotics carry the risk of addiction and side effects, such as constipation, nausea, confusion, vomiting, hallucinations, drowsiness, dizziness, headache, agitation, and insomnia. Further, narcotics may impair a patient's ability to undergo rehabilitation.

Electrical stimulation systems have been used for the relief of chronic pain, but widespread use of available systems for the treatment of postoperative pain is limited. There exist both external and implantable devices for providing electrical stimulation to activate nerves and/or muscles to provide therapeutic relief of pain. These "neurostimulators" are able to provide treatment and/or therapy to individual portions of the body. The operation of these devices typically includes the use of an electrode placed either on the external surface of the skin or a surgically implanted electrode. In most cases, surface electrode(s), cuff-style electrode(s), paddle-style electrode(s), or spinal column electrodes may be used to deliver electrical stimulation to the select portion of the patient's body.

One example of the neurostimulators identified above is transcutaneous electrical nerve stimulation (TENS). TENS has been cleared by the FDA for treatment of pain. TENS systems are external neurostimulation devices that use electrodes placed on the skin surface to activate target nerves below the skin surface. TENS has a low rate of serious complications.

Application of TENS has been used to treat pain with inconsistent results, and it has low patient compliance, because it may cause additional discomfort by generating cutaneous pain signals due to the electrical stimulation being applied through the skin. Additionally, the overall system is bulky and cumbersome. Further, TENS requires that surface electrodes be placed near the site of pain, which would be near the incision site for post-operative pain. This may impair healing or increase the risk of infection for the patient.

Moreover, several clinical and technical issues associated with surface electrical stimulation have prevented it from becoming a widely accepted treatment method. First, stimulation of cutaneous pain receptors oftentimes cannot be avoided resulting in stimulation-induced pain that limits patient tolerance and compliance. Second, it is difficult to stimulate deep nerves and/or muscles with surface electrodes without stimulating overlying, more superficial nerves and/or muscles resulting in unwanted stimulation. Finally, clinical skill and intensive patient training is required to place surface electrodes reliably on a daily basis and adjust stimulation parameters to provide optimal treatment. The required daily maintenance and adjustment of a surface electrical stimulation system is a major burden on both patient and caregiver.

Peripheral nerve stimulation may be effective in reducing pain, but it previously required specialized surgeons to place cuff- or paddle-style leads around the nerves in a time consuming procedure. This is particularly problematic to treat post-operative pain in that additional surgeries may be required to actually treat the pain—typically not a preferred approach, especially to treat pain following a separate surgery.

These above-mentioned methods of implementation have practical limitations that prevent widespread use.

Nevertheless, undergoing a surgical procedure, and recovering therefrom, is generally a painful process, emotionally and physically. There remains room in the art of surgical preparation and/or pain management for improved systems and methods to be used to ready an animal body for surgery and/or to assist in the recovery of the body after a surgical operation. There is, therefore, a need from an improved pain treatment system and method for relief of post-operative pain, especially pain following limb joint replacement surgery.

SUMMARY OF THE INVENTION

The invention provides systems and methods for placing one or more leads in tissues for providing electrical stimulation to tissue to treat pain in a manner unlike prior systems and methods.

The invention provides an electrical stimulation device having at least one percutaneous lead adapted for insertion within tissue of an animal body and a pulse generator operatively coupled with the at least one lead, wherein the pulse generator is configured to stimulate at least one nerve innervating a region of pain following the limb joint replacement surgery.

The invention further provides a kit for treatment of pain following limb joint replacement surgery having a needle insertable into an animal body tissue, at least one percutaneous electrode lead operatively inserted into the needle, wherein the needle and at least one percutaneous lead are inserted into an insertion point of the animal body, whereby the needle is removable from the animal body tissue and the at least one percutaneous electrode lead is retained within the animal body, and a pulse generator operatively coupled with the at least one electrode lead, wherein the pulse generator is configured to stimulate at least one nerve innervating a region of pain following a limb joint replacement surgery.

The invention also provides methods to alleviate pain following a limb joint replacement surgery including inserting at least one electrode within a therapeutically effective distance from at least one nerve, and applying electrical stimulation through the at least one electrode to affect the at least one nerve innervating a region of pain following the limb joint replacement surgery, wherein the electrical stimulation does not cause pain.

Other features and advantages of the inventions are set forth in the following specification and attached drawings.

BRIEF DESCRIPTION OF THE DRAWINGS

Operation of the invention may be better understood by reference to the detailed description taken in connection with the following illustrations, wherein:

FIGS. 13A, 13B, and 13C are schematic sectional anatomic views of a system for applying peripheral nerve stimulation along a sciatic/tibial nerve.

FIG. 14 is a frontal view showing the peripheral nerve stimulation system and TKA incision.

FIG. 16 is a view of the areas of pain and paresthesia on a diagram of the body.

DETAILED DESCRIPTION

Reference will now be made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the following description is presented by way of illustration only and should not limit in any way the various alternatives and modifications that may be made to the illustrated embodiments and still be within the spirit and scope of the invention.

Any elements described herein as singular can be pluralized (i.e., anything described as "one" can be more than one). Any species element of a genus element can have the characteristics or elements of any other species element of that genus. The described configurations, elements or complete assemblies and methods and their elements for carrying out the invention, and variations of aspects of the invention can be combined and modified with each other in any combination.

1. The Peripheral Nervous System

Anatomic Overview

Figure 1A:
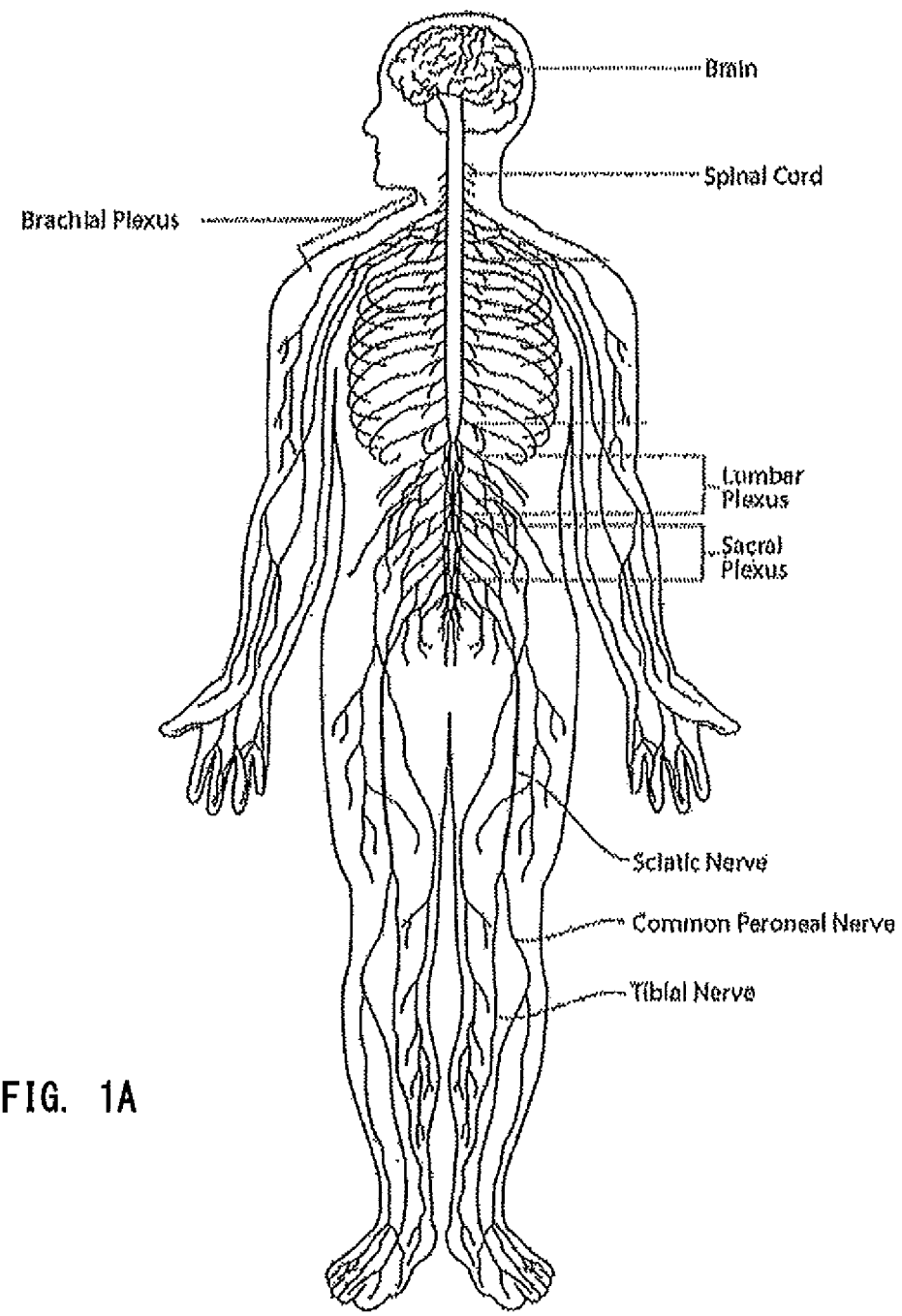
FIGS. 1A and 1B are schematic anatomic views, respectively anterior and lateral, of a human peripheral nervous system.
Figure 1B:
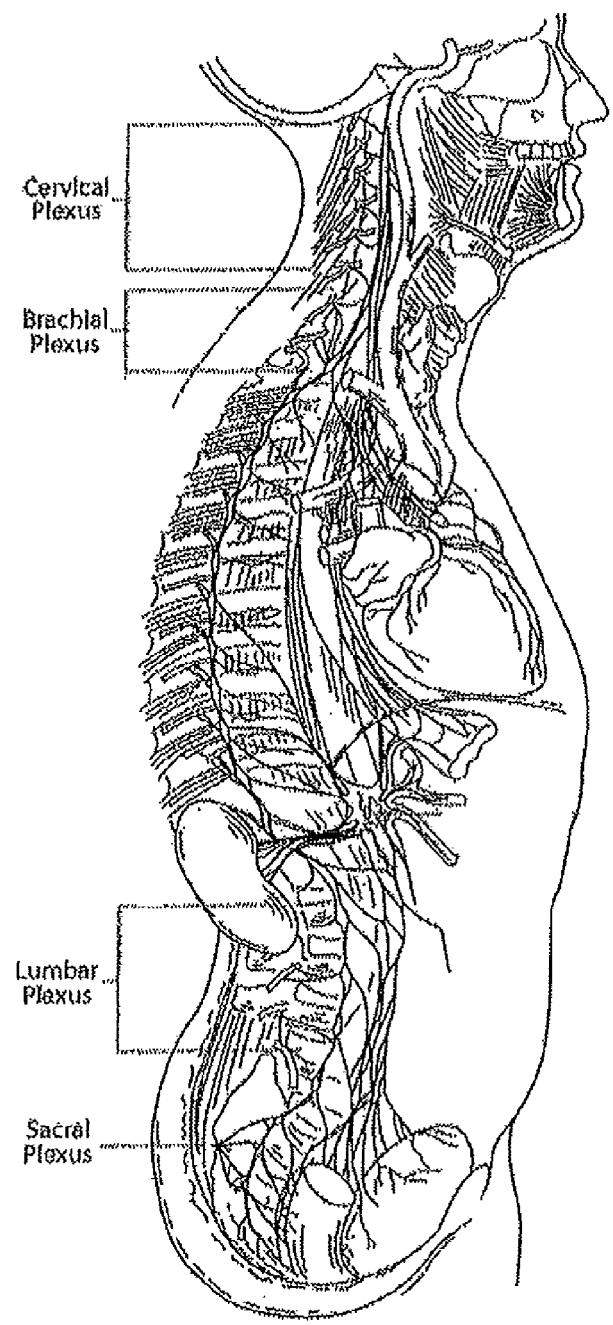

As generally shown in FIGS. 1A and 1B, the peripheral nervous system consists of nerve fibers and cell bodies outside the central nervous system (the brain and the spinal column) that conduct impulses to or away from the central nervous system. The peripheral nervous system is made up of nerves (called spinal nerves) that connect the central nervous system with peripheral structures. The spinal nerves of the peripheral nervous system arise from the spinal column and exit through intervertebral foramina in the vertebral column (spine). The afferent, or sensory, fibers of the peripheral nervous system convey neural impulses to the central nervous system from the sense organs (e.g., the eyes) and from sensory receptors in various parts of the body (e.g., the skin, muscles, etc.). The efferent, or motor, fibers convey neural impulses from the central nervous system to the effector organs (muscles and glands).

The somatic nervous system (SNS) is the part of the peripheral nervous system associated with the voluntary control of body movements through the action of skeletal muscles, and with reception of external stimuli, which helps keep the body in touch with its surroundings (e.g., touch, hearing, and sight). The system includes all the neurons connected with skeletal muscles, skin and sense organs. The somatic nervous system consists of efferent nerves responsible for sending central nervous signals for muscle contraction. A somatic nerve is a nerve of the somatic nervous system.

A. Spinal Nerves

A typical spinal nerve arises from the spinal cord by rootlets which converge to form two nerve roots, the dorsal (sensory) root and the ventral (motor) root. The dorsal and ventral roots unite into a mixed nerve trunk that divides into a smaller dorsal (posterior) primary ramus and a much larger ventral (anterior) primary ramus. The posterior primary rami serve a column of muscles on either side of the vertebral column, and a narrow strip of overlying skin. All of the other muscle and skin is supplied by the anterior primary rami.

Figure 2:
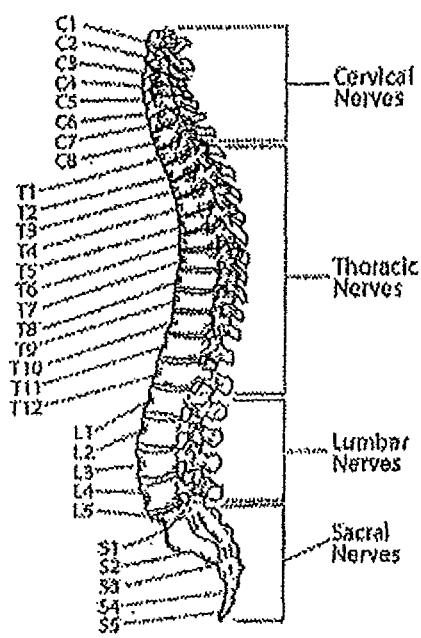
FIG. 2 is a schematic anatomic view of a human spine, showing the various regions and the vertebrae comprising the regions.

The nerve roots that supply or turn into peripheral nerves can be generally categorized by the location on the spine where the roots exit the spinal cord, i.e., as generally shown in FIG. 2, cervical (generally in the head/neck, designated C1 to C8), thoracic (generally in chest/upper back, designated T1 to T12), lumbar (generally in lower back, designated L1 to L5); and sacral (generally in the pelvis, designated S1 to S5). All peripheral nerves can be traced back (proximally toward the spinal column) to one or more of the spinal nerve roots in either the cervical, thoracic, lumbar, or sacral regions of the spine. The neural impulses comprising pain felt in a given muscle or cutaneous region of the body pass through spinal nerves and (usually) one or more nerve plexuses. The spinal nerves begin as roots at the spine, and can form trunks that divide by divisions or cords into branches that innervate skin and muscles.

B. Nerves of the Sacral Plexus

The sacral plexus provides motor and sensory nerves for the posterior thigh, most of the lower leg, and the entire foot.

1. The Sciatic Nerve

Figure 4:
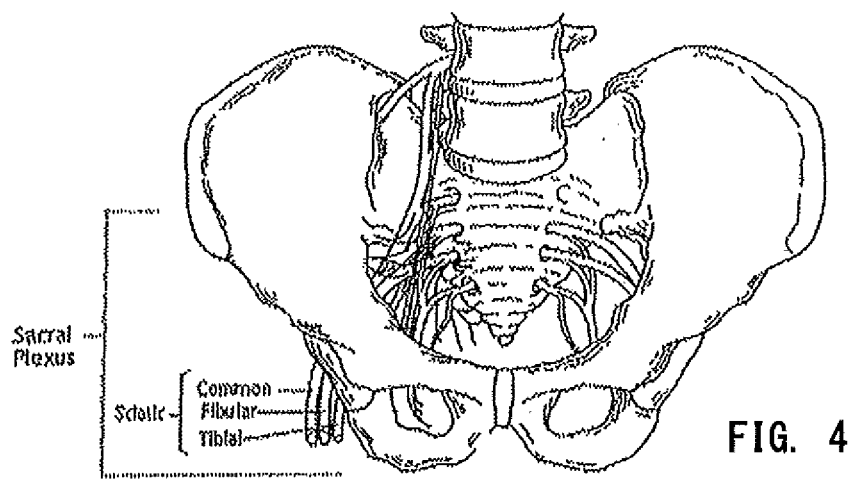
FIG. 4 is an anatomic view of the spinal nerves of the sacral plexus.
Figure 5:
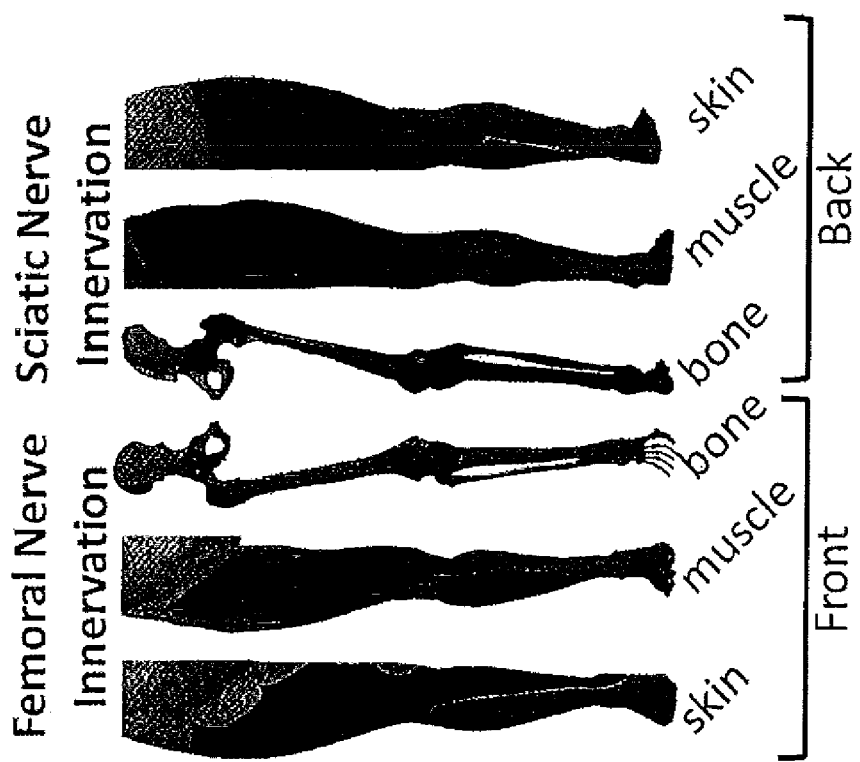
FIG. 5 is an anatomic view of the femoral nerve and sciatic nerve innervation of the leg.

As shown in FIGS. 1A and 4, the sciatic nerve (also known as the ischiatic nerve) arises from the sacral plexus. It begins in the lower back and runs through the buttock and down the lower limb. The sciatic nerve supplies nearly the whole of the skin of the leg, the muscles of the back of the thigh, and those of the leg and foot. It is derived from spinal nerves L4 through S3. It contains fibers from both the anterior and posterior divisions of the lumbosacral plexus.

The nerve gives off articular and muscular branches. The articular branches (rami articulares) arise from the upper part of the nerve and supply the hip-joint, perforating the posterior part of its capsule; they are sometimes derived from the sacral plexus. The muscular branches (rami musculares) innervate the following muscles of the lower limb: biceps femoris, semitendinosus, semimembranosus, and adductor magnus. The nerve to the short head of the biceps femoris comes from the common peroneal part of the sciatic, while the other muscular branches arise from the tibial portion, as may be seen in those cases where there is a high division of the sciatic nerve.

The muscular branch of the sciatic nerve eventually gives off the tibial nerve (shown in FIG. 1A) and common peroneal nerve (also shown in FIG. 1A), which innervates the muscles of the (lower) leg. The tibial nerve innervates the gastrocnemius, popliteus, soleus and plantaris muscles and the knee joint. It also goes on to innervate all muscles of the foot except the extensor digitorum brevis (which is innervated by the peroneal nerve).

C. Nerves of the Lumbar Plexus

Figure 3:
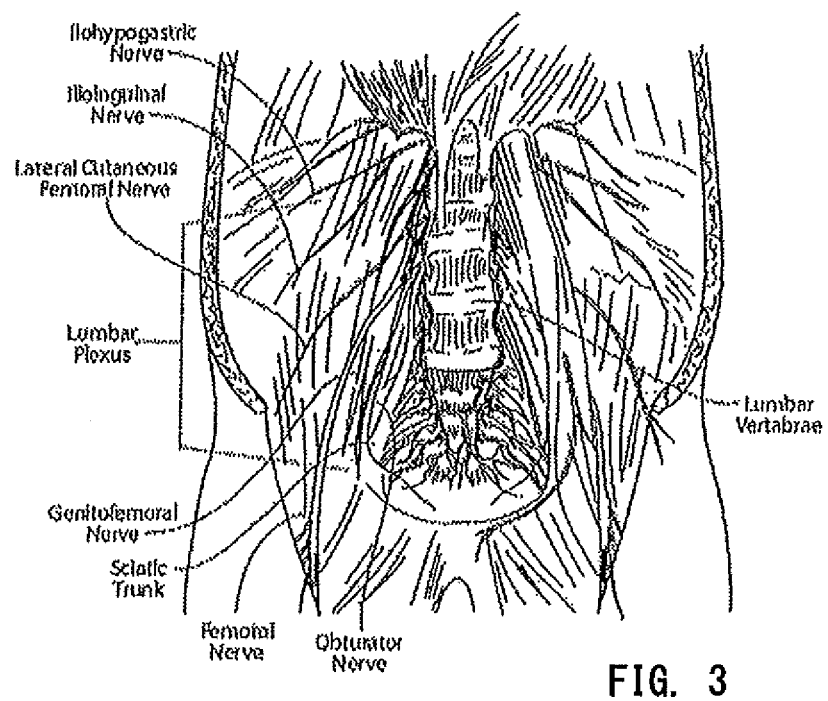
FIG. 3 is an anatomic view of the spinal nerves of the lumbar plexus.

The lumbar plexus (see FIG. 3) provides motor, sensory, and autonomic fibers to gluteal and inguinal regions and to the lower extremities. The gluteal muscles are the three muscles that make up the buttocks: the gluteus maximus muscle, gluteus medius muscle and gluteus minimus muscle. The inguinal region is situated in the groin or in either of the lowest lateral regions of the abdomen.

1. The Iliohypogastric Nerve

The iliohypogastric nerve (see FIG. 3) runs anterior to the psoas major on its proximal lateral border to run laterally and obliquely on the anterior side of quadratus lumborum. Lateral to this muscle, it pierces the transversus abdominis to run above the iliac crest between that muscle and abdominal internal oblique. It gives off several motor branches to these muscles and a sensory branch to the skin of the lateral hip. Its terminal branch then runs parallel to the inguinal ligament to exit the aponeurosis of the abdominal external oblique above the external inguinal ring where it supplies the skin above the inguinal ligament (i.e. the hypogastric region) with the anterior cutaneous branch.

2. The Ilioinguinal Nerve

The ilioinguinal nerve (see FIG. 3) closely follows the iliohypogastric nerve on the quadratus lumborum, but then passes below it to run at the level of the iliac crest. It pierces the lateral abdominal wall and runs medially at the level of the inguinal ligament where it supplies motor branches to both transversus abdominis and sensory branches through the external inguinal ring to the skin over the pubic symphysis and the lateral aspect of the labia majora or scrotum.

3. The Lateral Cutaneous Femoral Nerve

The lateral cutaneous femoral nerve (see FIG. 3) pierces psoas major on its lateral side and runs obliquely downward below the iliac fascia. Medial to the anterior superior iliac spine it leaves the pelvic area through the lateral muscular lacuna. In the thigh it briefly passes under the fascia lata before it breaches the fascia and supplies the skin of the anterior thigh.

4. The Obturator Nerve

The obturator nerve (see FIG. 3) leaves the lumbar plexus and descends behind psoas major on it medial side, then follows the linea terminalis and exits through the obturator canal. In the thigh, it sends motor branches to obturator externus before dividing into an anterior and a posterior branch, both of which continue distally. These branches are separated by adductor brevis and supply all thigh adductors with motor innervation: pectineus, adductor longus, adductor brevis, adductor magnus, adductor minimus, and gracilis. The anterior branch contributes a terminal, sensory branch which passes along the anterior border of gracilis and supplies the skin on the medial, distal part of the thigh.

5. The Femoral Nerve

The femoral nerve (see FIG. 3 and also FIG. 10A) is the largest and longest nerve of the lumbar plexus. It gives motor innervation to iliopsoas, pectineus, sartorius, and quadriceps femoris; and sensory innervation to the anterior thigh, posterior lower leg, and hindfoot. It runs in a groove between psoas major and iliacus giving off branches to both muscles. In the thigh it divides into numerous sensory and muscular branches and the saphenous nerve, its long sensory terminal branch which continues down to the foot.

The femoral nerve has anterior branches (intermediate cutaneous nerve and medial cutaneous nerve) and posterior branches. The saphenous nerve (branch of the femoral nerve) provides cutaneous (skin) sensation in the medial leg. Other branches of the femoral nerve innervate structures (such as muscles, joints, and other tissues) in the thigh and around the hip and knee joints. As an example, branches of the femoral nerve innervate the hip joint, knee joint, and the four parts of the Quadriceps femoris (muscle): Rectus femoris (in the middle of the thigh) originates on the ilium and covers most of the other three quadriceps muscles. Under (or deep to) the rectus femoris are the other 3 of the quadriceps muscles, which originate from the body of the femur. Vastus lateralis (on the outer side of the thigh) is on the lateral side of the femur. Vastus medialis (on the inner part thigh) is on the medial side of the femur. Vastus intermedius (on the top or front of the thigh) lies between vastus lateralis and vastus medialis on the front of the femur. Branches of the femoral nerve often innervate the pectineus and sartorius muscles.

II. The System

Figure 7:
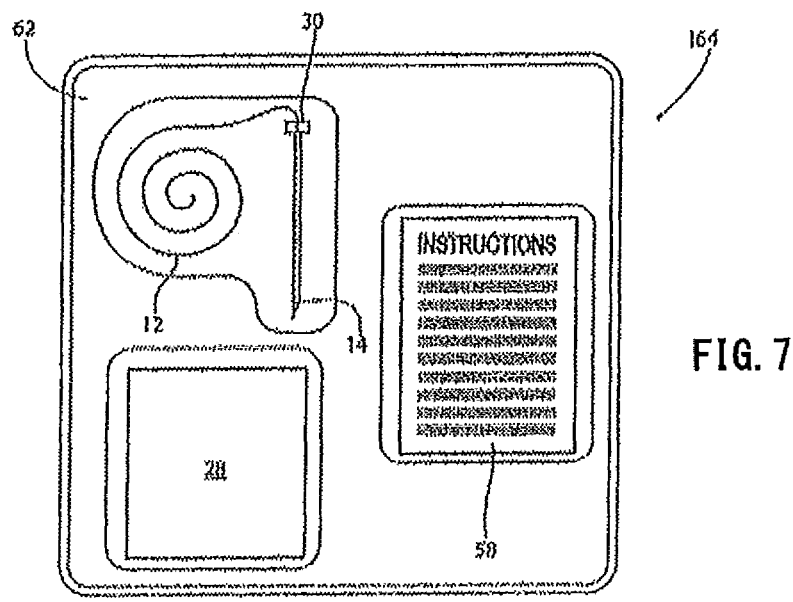
FIG. 7 is a view of a package containing a peripheral nerve stimulation system.
Figure 8A:
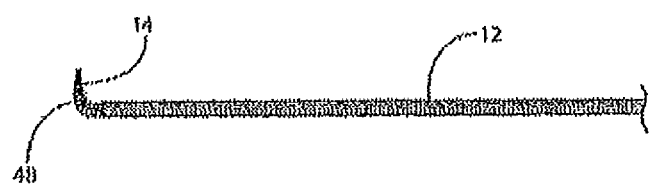
FIGS. 8A/B and 9A/B are representative leads that can form a part of a peripheral nerve stimulation system.
Figure 8B:

Shown in FIG. 7 is an electrical stimulation device 164 configured to treat post-operative pain, especially pain following limb joint replacement surgery. Here, a limb joint replacement surgery is defined to include a shoulder, elbow, wrist, finger joint, hip, knee, ankle and toe joint, but to exclude the back, neck and head. The electrical stimulation device may include one or more leads 12 having one or more electrodes 14 adapted for insertion into in any tissue of the body in electrical proximity but away from nerves. This location of leads 12 may improve recruitment of targeted nerves for therapeutic purposes, such as for the treatment of pain. It is to be appreciated that the present electrical stimulation device is intended only to treat regions of pain that include any limbs or joint replacements, including arms and legs in both humans and animals.

A. Stimulation of Peripheral Nerves

FIGS. 15A-15D show a peripheral nerve system and method that incorporates features of the present teachings. As shown in FIGS. 15A-15D, the system and method may identify a region where there is a local manifestation of pain. The region of pain may comprise any appropriate portion of the body, e.g., tissue, skin, bone, a joint, or muscle. The system and method may identify one or more spinal nerves located distant from the region where pain is manifested, through which neural impulses comprising the pain pass. A given spinal nerve that is identified may comprise a nerve trunk located in a nerve plexus, or a division and/or a cord of a nerve trunk, or a nerve branch, or a nerve plexus provided that it is upstream or cranial of where the nerve innervates the region affected by the pain. The given spinal nerve may be identified by medical professionals using textbooks of human anatomy along with their knowledge of the site and the nature of the pain or injury, as well as by physical manipulation and/or imaging, e.g., by ultrasound, fluoroscopy, or X-ray examination, of the region where pain is manifested. A desired criteria of the selection may include identifying the location of tissue in a therapeutically effective distance from the nerve or passage, which tissue may be accessed by placement of one or more stimulation electrodes, aided if necessary by ultrasonic or electro-location techniques. A therapeutically effective distance may be defined to mean the placement of a lead either in contact with, or more preferably adjacent to a nerve. The nerve identified may comprise a targeted peripheral nerve. The tissue identified may comprise the "targeted tissue."

The electrodes 14 of the electrical stimulation device 164 may be percutaneously inserted using percutaneous leads 12. The system and method may place the one or more leads 12(B) with its electrode 14(B) in the targeted tissue in electrical proximity to but spaced away from the targeted peripheral nerve. The system and method may apply electrical stimulation through the one or more stimulation electrodes 14(B) to electrically activate or recruit the targeted peripheral nerve that conveys the neural impulses comprising the pain to the spinal column.

The system and method may apply electrical stimulation to peripheral nerves throughout the body. By way of a non-limiting example, the peripheral nerves may comprise one or more spinal nerves in the brachial plexus, to treat pain in the shoulders (see FIG. 15C), arms and hands (see FIG. 15D); and/or one or more spinal nerves in the lumbar plexus, to treat pain in the thighs, knees, and calves (see FIGS. 15A and 15B); and/or one or more spinal nerves in the sacral plexus, to treat pain in the thighs, calves, and feet (see FIGS. 15A and 15B); and/or one or more spinal nerves in the cervical plexus, to treat pain in the shoulders (see FIG. 15C).

For example, if the pinky finger is the location of pain following a limb joint replacement surgery, the system and method may identify and stimulate the ulnar nerve at a location upstream or cranial of where the nerve innervates the muscle or skin of the pinky finger, e.g., in the palm of the hand, forearm, and/or upper arm. If electrical stimulation activates the target peripheral nerve sufficiently at the correct intensity, then the patient will feel a comfortable tingling sensation called paresthesia in the same region as their pain, which overlaps with the region of pain and/or otherwise reduce pain.

It is to be appreciated that the sensation could be described with other words such as buzzing, thumping, etc. Evoking paresthesia in the region of pain confirms correct lead placement and indicates stimulus intensity is sufficient to reduce pain. Inserting a lead 12 percutaneously may allow the lead 12 to be placed quickly and easily. Placing the lead 12 in a peripheral location, i.e., tissue, where it is less likely to be dislodged, may address lead migration problems of spinal cord stimulation that may otherwise cause decreased paresthesia coverage, decreased pain relief, and the need for frequent patient visits for reprogramming.

Placing the lead 12 percutaneously in tissue in electrical proximity to but spaced away from the targeted peripheral nerve may also minimize complications related to lead placement and movement. In a percutaneous system, an electrode lead 12, such as a coiled fine wire electrode lead may be used because it is minimally-invasive and well suited for placement in proximity to a peripheral nerve. The lead may be sized and configured to withstand mechanical forces and resist migration during long-term use, particularly in flexible regions of the body, such as the shoulder, elbow, and knee.

Figure 6A:
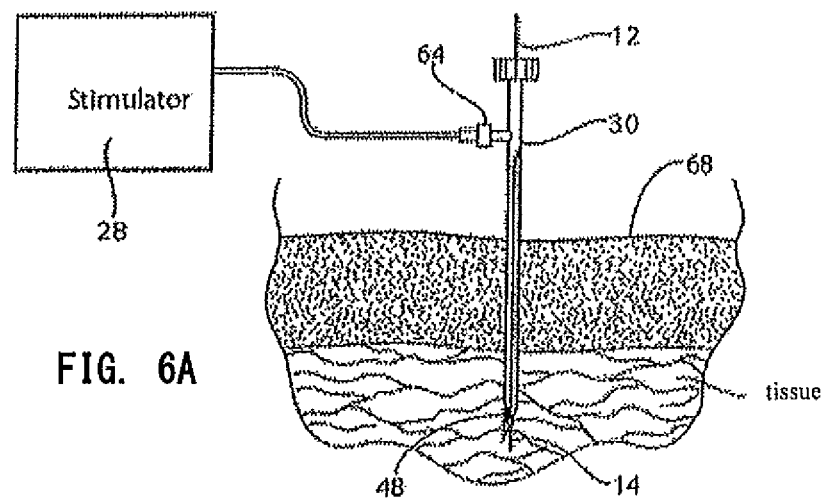
FIGS. 6A to 6C are views showing a percutaneous lead that can form a part of a peripheral nerve stimulation system.
Figure 6B:
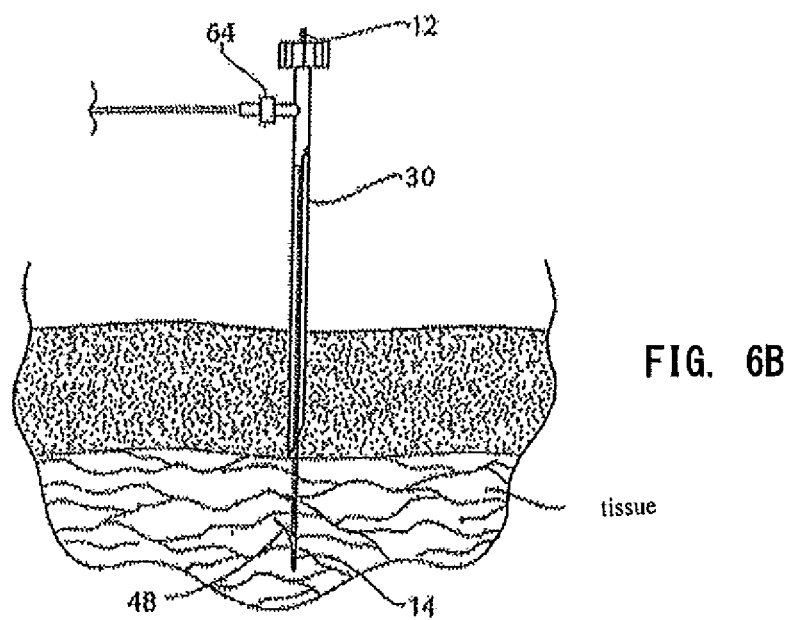
Figure 6C:
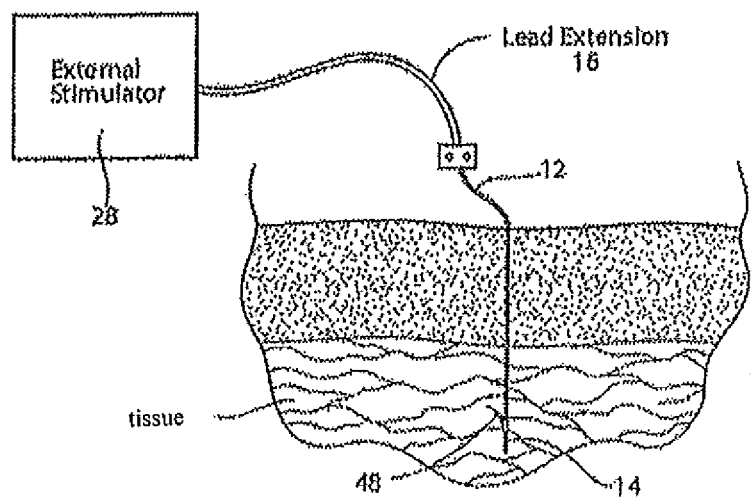

As FIG. 6A shows, the electrode lead may include a fine wire electrode 14, paddle electrode, intramuscular electrode, or general-purpose electrode, inserted via a needle introducer 30 or surgically implanted in proximity of a targeted peripheral nerve. Once proper placement is confirmed, the needle introducer 30 may be withdrawn (as FIGS. 6B and 6C show), leaving the electrode 14 in place. Stimulation may also be applied through a penetrating electrode, such as an electrode array comprised of any number (i.e., one or more) of needle-like electrodes that may be inserted into the target site. In both cases, the lead may be placed using a needle-like introducer 30, allowing the lead/electrode placement to be minimally invasive. In a representative embodiment, the lead 12 may include a thin, flexible component made of a metal and/or polymer material. By "thin," it is contemplated that the lead may not be greater than about 0.75 mm (0.030 inch) in diameter. However, the present teachings are not limited to such dimensions. Any appropriate lead 12 may be utilized. The lead 12 may also include one or more coiled metal wires with in an open or flexible elastomer core. The wire may be insulated, e.g., with a biocompatible polymer film, such as polyfluorocarbon, polyimide, or parylene. The lead 12 may be electrically insulated everywhere except at one (monopolar), or two (bipolar), or three (tripolar), for example, conduction locations near its distal tip. Each of the conduction locations may be connected to one or more conductors that may run the length of the lead and lead extension 16 (see FIG. 6C) or a portion thereof. The conductor may provide electrical continuity from the conduction location through the lead 12 to an external pulse generator or stimulator 28 (see FIG. 6C).

The conduction location or electrode 14 may include a de-insulated area of an otherwise insulated conductor that may run the length of an entirely insulated electrode or a portion thereof. The de-insulated conduction region of the conductor may be formed differently, e.g., it may be wound with a different pitch, or wound with a larger or smaller diameter, or molded to a different dimension. The conduction location or the electrode 14 may include a separate material (e.g., metal or a conductive polymer) exposed to the body tissue to which the conductor of the wire is bonded.

The lead 12 may be provided in a sterile package 62 (see FIG. 7), and may be pre-loaded in the introducer needle 30. Alternatively, the lead may be introduced via the same needle that is used to inject anesthetic or analgesics during peripheral nerve blocks, which are often used post-limb joint replacement surgery. The package 62 may take various forms and the arrangement and contents of the package 62 may be as appropriate related to the use thereof. As shown in FIG. 7, the package 62 may include a sterile, wrapped assembly. The package 62 may include an interior tray made from any appropriate material, e.g., from die cut cardboard, plastic sheet, or thermo-formed plastic material, which may hold the contents. The package 62 may also desirably include instructions for use 58 regarding using the contents of the package to carry out the lead 12 location and placement procedures, as will be described in greater detail below.

The lead 12 may possess mechanical properties in terms of flexibility and fatigue life that provide an operating life free of mechanical and/or electrical failure, taking into account the dynamics of the surrounding tissue (i.e., stretching, bending, pushing, pulling, crushing, etc.). The material of the electrode 14 may discourage the in-growth of connective tissue along its length or an applicable portion thereof, so as not to inhibit its withdrawal at the end of its use. However, it may be desirable to encourage the in-growth of connective tissue at the distal tip of the electrode 14, to enhance its anchoring in tissue.

Figure 12A:
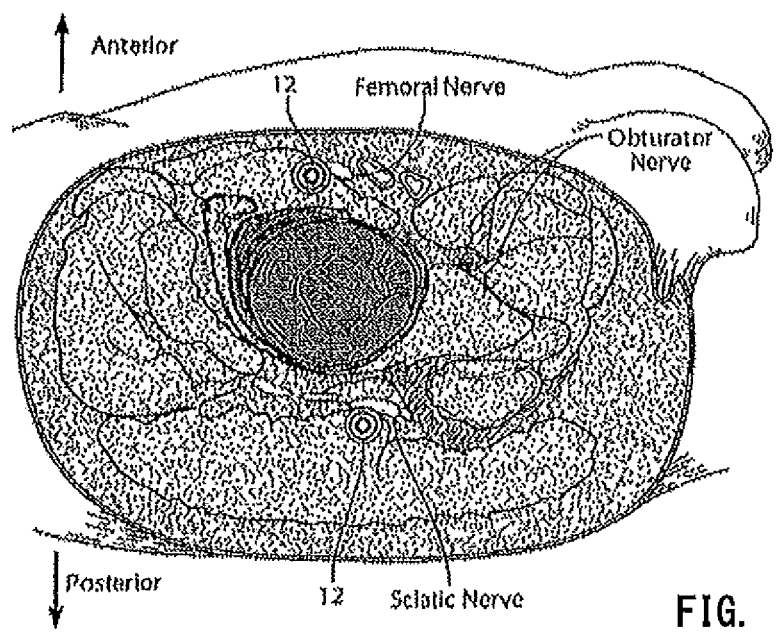
FIGS. 12A and 12B are schematic sectional anatomic views of systems for applying peripheral nerve stimulation to a femoral nerve and a sciatic/tibial nerve.

Embodiments of the lead 12 shown in FIG. 12A may include a minimally invasive coiled fine wire lead 12 and electrode 14. The electrode 14 may also include, at its distal tip, an anchoring element 48. In the illustrated embodiments, the anchoring element 48 may take the form of a simple barb or bend (see also FIG. 6C).

The anchoring element 48 may be sized and configured so that, when in contact with tissue, it takes purchase in tissue, to resist dislodgement or migration of the electrode 14 out of the correct location in the surrounding tissue. Desirably, the anchoring element 48 may be prevented from fully engaging body tissue until after the electrode 14 has been correctly located and deployed.

Alternative embodiments of the electrode lead 12 shown in FIGS. 9A and 9B may also include, at or near its distal tip or region, one or more anchoring element(s) 70. In the illustrated embodiments, the anchoring element 70 may take the form of an array of shovel-like paddles or scallops 76 proximal to the proximal-most electrode 14 (although a paddle 76 or paddles may also be proximal to the distal most electrode 14, or may also be distal to the distal most electrode 14). The paddles 76 as shown may be sized and configured so they will not cut or score the surrounding tissue. The anchoring element 70 may be sized and configured so that, when in contact with tissue, it takes purchase in tissue, to resist dislodgement or migration of the electrode out of the correct location in the surrounding tissue (e.g., muscle 54). The anchoring element 70 may be prevented from fully engaging body tissue until after the electrode 14 has been deployed. The electrode 14 may not be deployed until after it has been correctly located during the implantation (lead placement) process, as previously described. In addition, the lead 12 may include one or more ink markings 74, 75 (shown in FIG. 9A) to aid the clinician in its proper placement.

Alternatively, or in combination, stimulation may be applied through any type of nerve cuff (spiral, helical, cylindrical, book, flat interface nerve electrode (FINE), slowly closing FINE, etc.), paddle (or paddle-style) electrode lead, cylindrical electrode lead, echogenic needle (i.e., visible under ultrasound) and/or other lead that is surgically or percutaneously placed within tissue at the target site.

The lead 12 may exit through the skin and connect with one or more external stimulators 28 (this approach is shown in FIG. 6C). Further, the lead 12 may be connected as needed to internal and external coils for RF (Radio Frequency) wireless telemetry communications or an inductively coupled telemetry to control the implanted pulse generator 28. The implanted pulse generator 28 may be located some distance (remote) from the electrode 14, or an implanted pulse generator may be integrated with an electrode(s) (not shown), eliminating the need to route the lead subcutaneously to the implanted pulse generator.

The introducer 30 (see FIG. 6A) may be insulated along the length of the shaft, except for those areas that correspond with the exposed conduction surfaces of the electrode 14 housed inside the introducer 30. These surfaces on the outside of the introducer 30 may be electrically isolated from each other and from the shaft of the introducer 30. These surfaces may be electrically connected to a connector 64 at the end of the introducer body (see FIG. 6A). This may allow connection to an external stimulator 28 (shown in FIG. 6A) during the implantation process. Applying stimulating current through the outside surfaces of the introducer 30 may provide a close approximation to the response that the electrode 14 will provide when it is deployed at the current location of the introducer 30.

The introducer 30 may be sized and configured to be bent by hand prior to its insertion through the skin. This may allow the physician to place the lead 12 in a location that is not in an unobstructed straight line with the insertion site. The construction and materials of the introducer 30 may allow bending without interfering with the deployment of the lead 12 and withdrawal of the introducer 30, leaving the lead 12 in the tissue.

Representative lead insertion techniques will now be described to place an electrode lead 12 in a desired location in tissue in electrical proximity to but spaced away from a peripheral nerve. It is this lead placement that may make possible the stimulation of the targeted nerve or peripheral nerves with a single lead 12 to provide pain relief.

To determine the optimal placement for the lead 12, test stimulation may be delivered through needle electrodes. Needle electrodes may be used because they may be easily repositioned until the optimal location to deliver stimulation is determined. A test needle may be used to generate paresthesia.

At least one lead(s) may be placed in tissue near a targeted peripheral nerve. The lead may be inserted via the introducer 30 in any appropriate manner, which may be similar in size and shape to a hypodermic needle. The introducer 30 may be any size. By way of a non-limiting example, the introducer 30 may range in size from 17 gauge to 26 gauge. Before inserting the introducer 30, the insertion site may be cleaned with a disinfectant (e.g., Betadine, 2% Chlorhexidine/80% alcohol, 10% povidone-iodine, or similar agent). A local anesthetic(s) may be administered topically and/or subcutaneously to the area in which the electrode and/or introducer will be inserted.

The position of the electrodes may be checked by imaging techniques, such as ultrasound, fluoroscopy, or X-rays. Following placement of the lead(s), the portion of the leads which exit the skin may be secured to the skin using covering bandages and/or adhesives.

Electrical stimulation may be applied to the targeted peripheral nerve during and after placement of the electrode. This may be used to determine whether stimulation of the targeted peripheral nerve can generate comfortable sensations or paresthesia that overlap with the region of pain and/or reduce pain.

In a percutaneous system 10 (as FIGS. 6A to 6C) shown, the lead 12 may be percutaneously placed near the targeted peripheral nerve and exit at a skin puncture site 16. A trial or screening test may be conducted in any appropriate clinical setting (e.g., an office of a clinician, a laboratory, a procedure room, an operating room, an intensive care unit, an acute rehabilitation facility, a subacute rehabilitation facility, etc.). During the trial, the lead 12 may be coupled to an external pulse generator 28 and temporary percutaneous and/or surface return electrodes, to confirm paresthesia coverage and/or pain relief of the painful areas.

If the clinical screening test is successful, the patient may proceed to treatment with an external pulse generator 28 (as shown in FIG. 6C) and temporary percutaneous and/or surface return electrodes. The treatment period may range from minutes to hours to days to weeks to months. By way of a non-limiting example, the treatment period may be between approximately three and 21 days.

Alternatively, a fully implanted pulse generator may be used if an external stimulator is considered too cumbersome for the patient.

Electrical stimulation may be applied between the lead and return electrodes (uni-polar mode). Regulated current may be used as a type of stimulation, but other type(s) of stimulation (e.g., non-regulated current such as voltage-regulated) may also be used. Multiple types of electrodes may be used, such as surface, percutaneous, and/or implantable electrodes. The surface electrodes may be a standard shape or they may be modified as appropriate to fit the contour of the skin.

In embodiments of a percutaneous system, the surface electrode(s) may serve as the anode(s) (or return electrode(s)), but the surface electrode(s) may be used as the cathode(s) (active electrode(s)) if necessary. When serving as a return electrode(s), the location of the electrode(s) may not be critical and may be positioned anywhere in the general vicinity, provided that the current path does not cross parts of the body (e.g., the heart), through which stimulation could be harmful.

The electrode lead may be placed via multiple types of approaches. By way of a non-limiting example, when the targeted peripheral nerve includes one or more nerves of the lumbar plexus or sacral plexus, the approach may be either a posterior (shown in FIG. 10A) or an anterior approach (shown in FIG. 11A). This may be similar to those used for regional anesthesia of the same targeted peripheral nerve, except that the approach may be used for placement through an introducer of stimulation lead(s) in electrical proximity to but spaced away from a peripheral nerve, and not for regional anesthesia. Unlike regional anesthesia, the approach to nerves of the lumbar plexus or sacral plexus may not involve the application of anesthesia to the nerve, and, when the introducer is withdrawn, the lead(s) may be left behind to desired stimulation of the target peripheral nerve.

In other embodiments, when the targeted peripheral nerve includes the sciatic nerve (see FIG. 12A), the introducer(s) 30 and/or lead(s) 12 may be directed towards the sciatic nerve using a posterior approach, such as the transgluteal approach or subgluteal approach, which are both well described and commonly used in regional anesthesiology. This approach may allow lead placement near a targeted peripheral nerve with a simple, quick (e.g., less than 10 minutes) procedure.

The landmarks for the transgluteal approach may include the greater trochanter and the posterior superior iliac spine. The introducer 30 may be inserted distal (e.g., approximately 2 cm to 6 cm, preferably 4 cm, in a preferred embodiment) to the midpoint between the greater trochanter and the posterior iliac spine. As a non-limiting example of patient positioning, the patient may be in a lateral decubitus position and tilted slightly forward. The landmarks for the subgluteal approach may include the greater trochanter and the ischial tuberosity. The introducer may be inserted distal (e.g., approximately 2 cm to 6 cm, preferably 4 cm, in the preferred embodiment) to the midpoint between the greater trochanter and the ischial tuberosity.

By way of a non-limiting example, when the targeted peripheral nerve includes the femoral nerve (see FIG. 12A), percutaneous leads 12 may be directed towards the femoral nerve using an anterior approach. The landmarks may include the inguinal ligament, inguinal crease, and femoral artery. The subject may be in the supine position with ipsilateral extremity slightly (approximately 10 to 20 degrees) abducted. The introducer may be inserted near the femoral crease but below the inguinal crease and approximately 1 cm lateral to the pulse of the femoral artery.

The size and shape of tissues, such as the buttocks, surrounding the target nerves may vary across subjects, and the approach may be modified as appropriate to accommodate various body sizes and shapes to access the target nerve.

Introducer placement may be guided by the individual's report of stimulus-evoked sensations (paresthesia) as the introducer is placed during test stimulation.

Figure 12B:
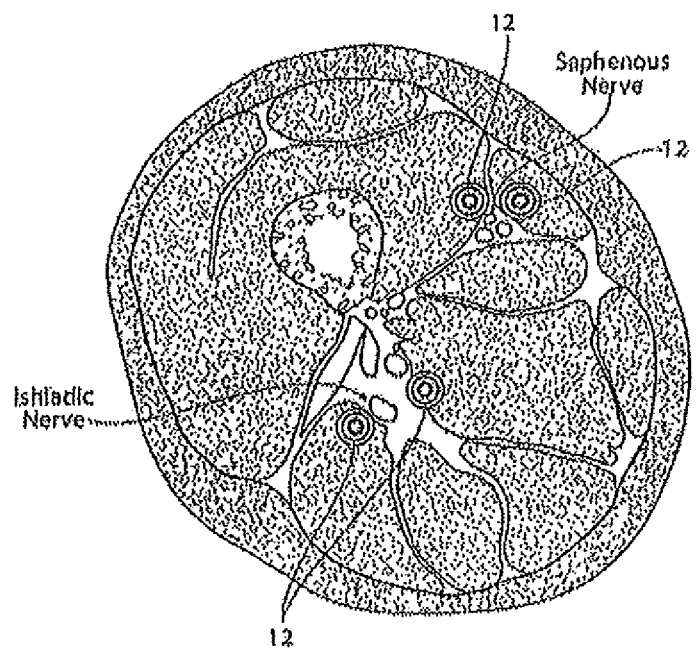
Figure 15A:
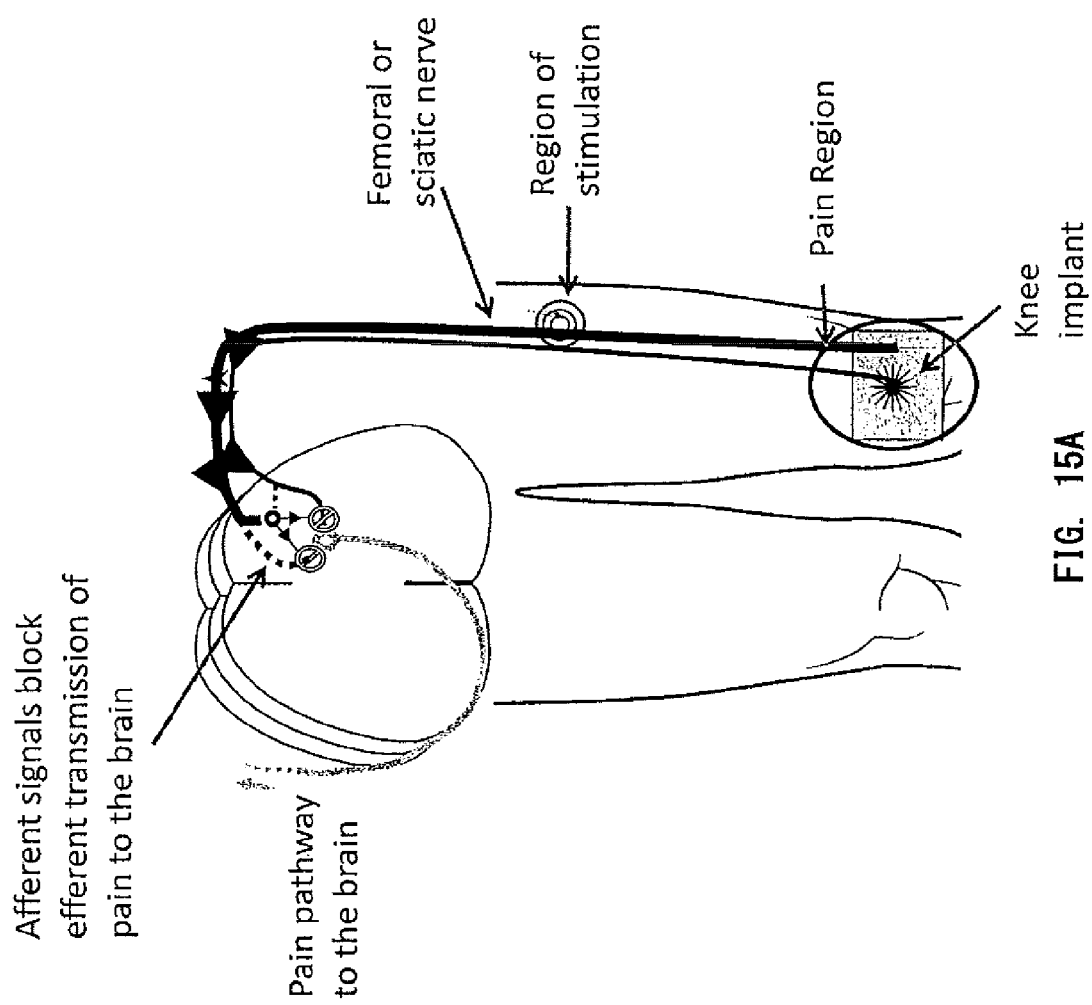
FIGS. 15A, 15B, 15C, and 15D are idealized, diagrammatic view showing peripheral nerve stimulation systems.
Figure 15B:
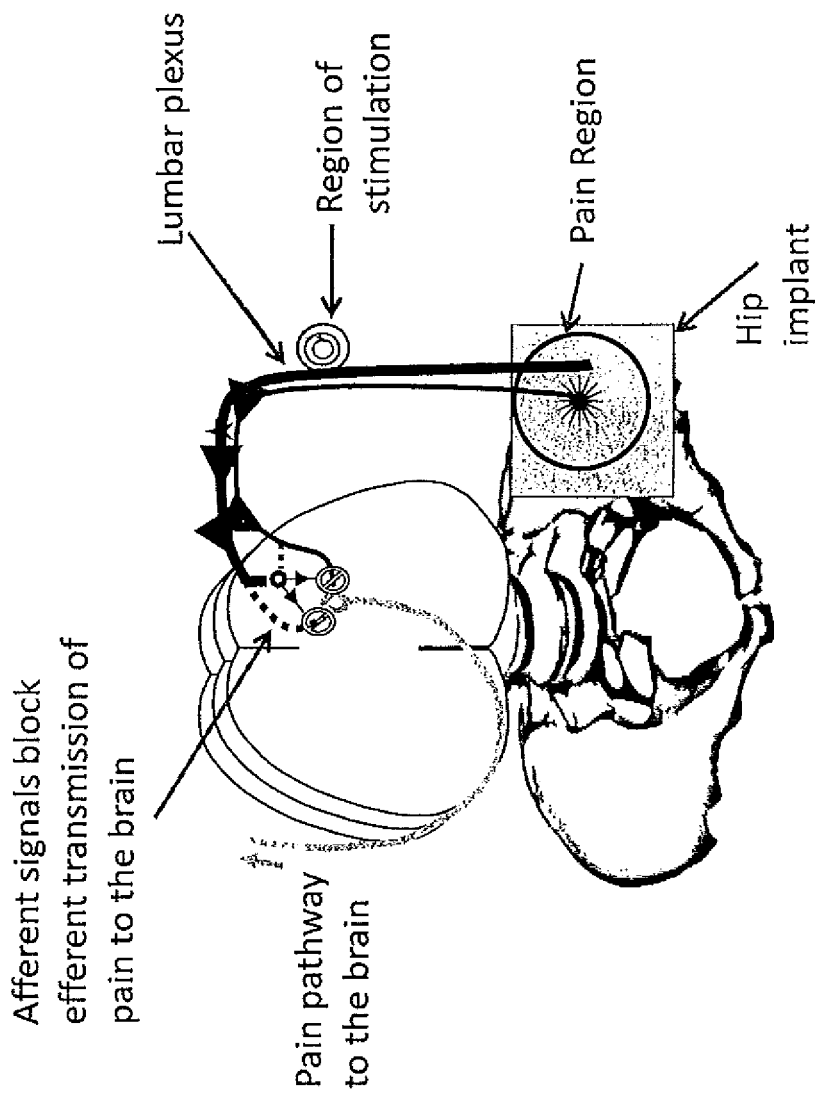
Figure 15C:
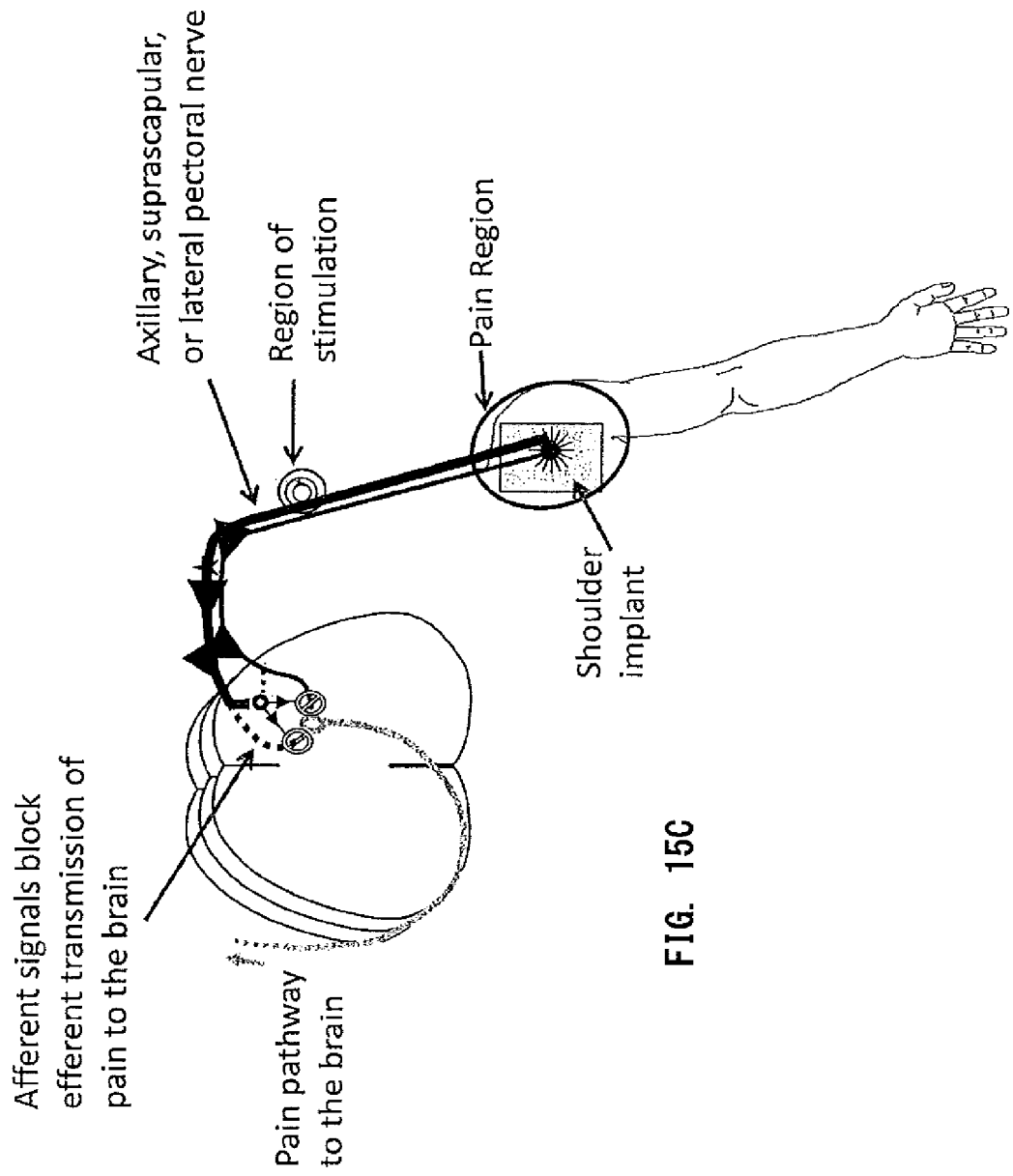
Figure 15D:
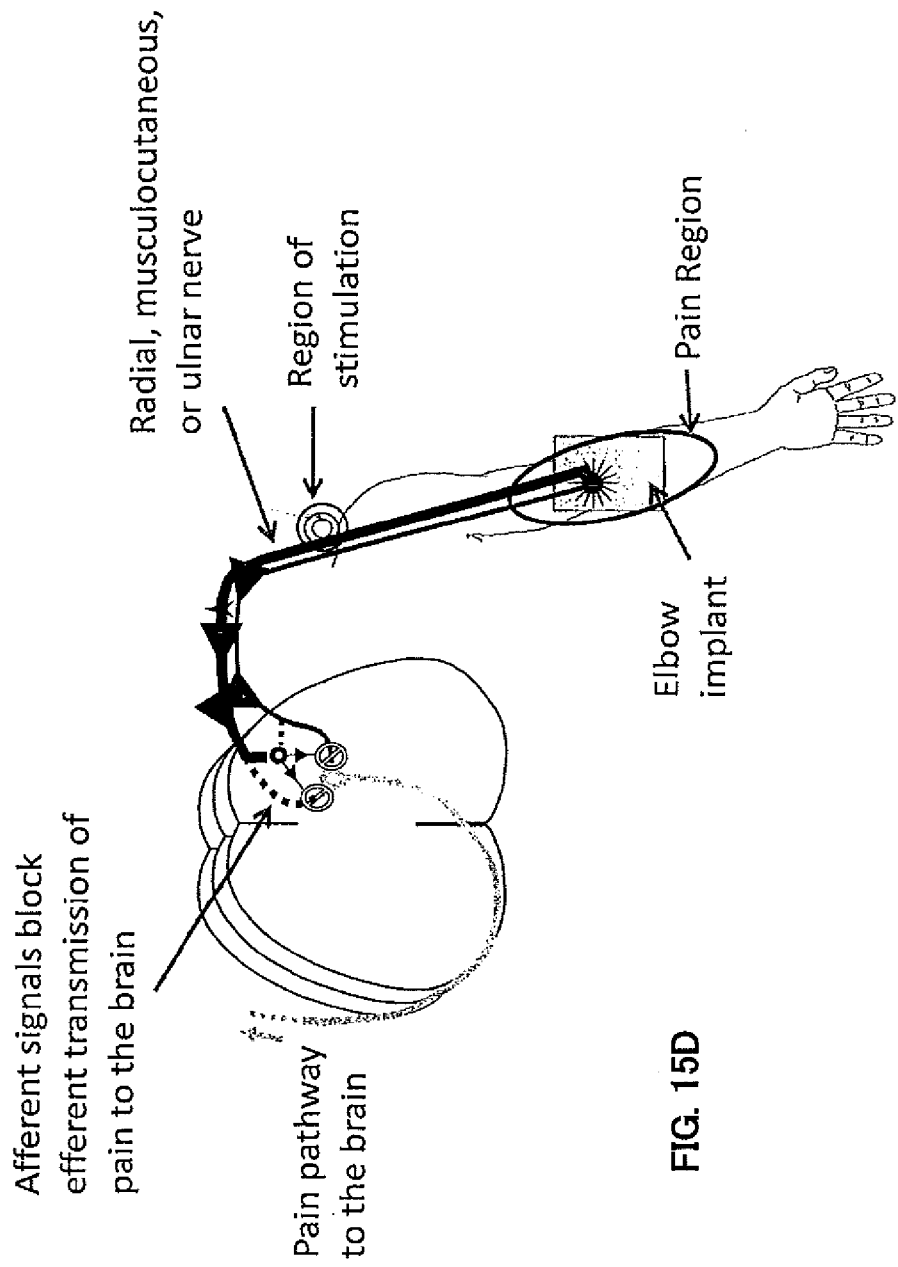

As shown in FIG. 12B, more than a single lead 12 may be placed around a given peripheral nerve, using either an anterior approach (e.g., femoral nerve) or a posterior approach (e.g., sciatic nerve). As FIGS. 13A, B, and C show, one or more leads 12 may be placed at different superior-inferior positions along a peripheral nerve and/or along different peripheral nerves.

Figures 10A, 10B:
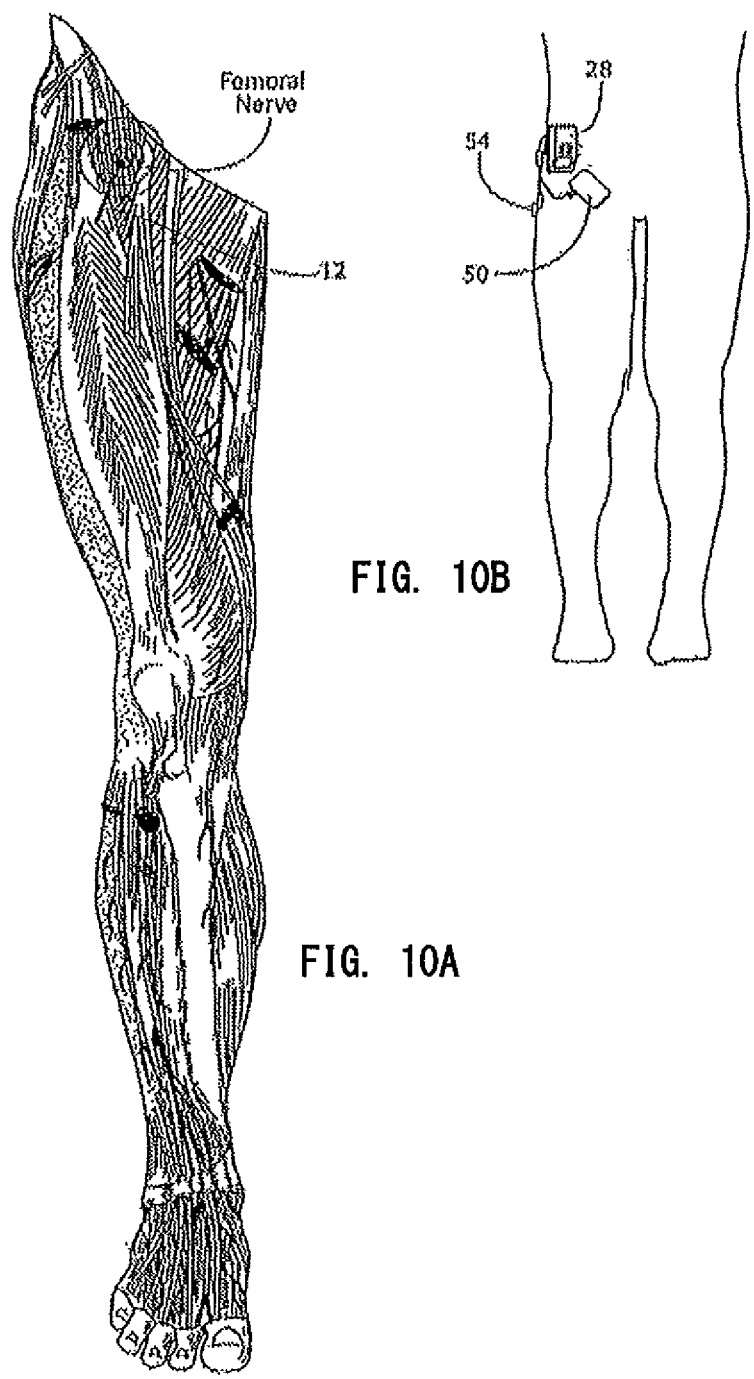
FIGS. 10A and 10B are schematic anatomic views of a system for applying peripheral nerve stimulation to a femoral nerve.
Figure 11A:
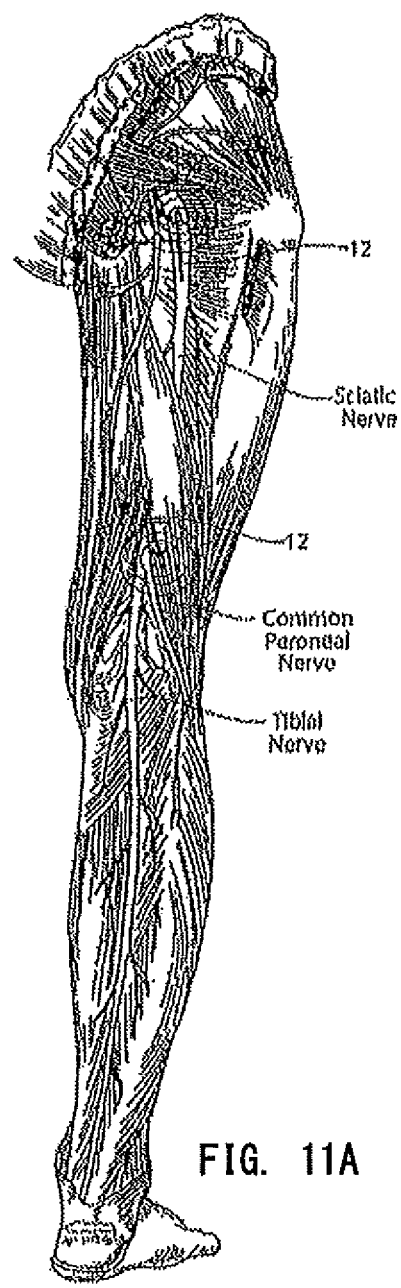
FIGS. 11A and 11B are schematic anatomic views of a system for applying peripheral nerve stimulation to a sciatic/tibial nerve.
Figure 11B:
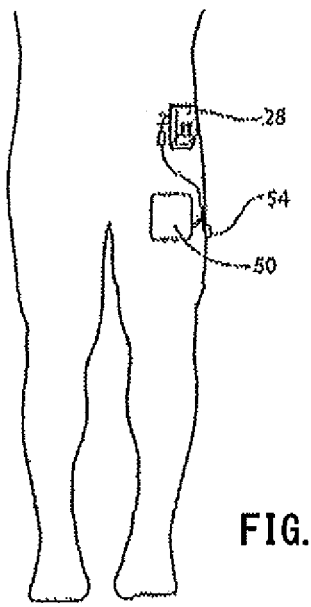

As FIGS. 10B (anterior approach, e.g., femoral nerve) and 11B (posterior approach, e.g., sciatic nerve) show, the lead 12 may be coupled to an external pulse generator 28 worn, e.g., on a belt, for a temporary stimulation regime. In this arrangement, the lead 12 may be covered with a bandage 50, and a surface electrode 54 may serve as a return electrode. The external/percutaneous system shown in FIGS. 10B and 10B may be replaced by an implanted system using an implanted pulse generator 60 and tunneled leads 62. In this arrangement, the case of the implanted pulse generator 60A may include the return electrode.

Control of the stimulator and stimulation parameters may be provided by one or more external controllers. Alternatively, a controller may be integrated with the external stimulator. The implanted pulse generator external controller (i.e., clinical programmer) may be a remote unit that uses RF (Radio Frequency) wireless telemetry communications (rather than an inductively coupled telemetry) to control the implanted pulse generator. The external or implantable pulse generator may use passive charge recovery to generate the stimulation waveform, regulated voltage (e.g., 10 mV to 20 V), and/or regulated current (e.g., about 10 mA to about 50 mA). Passive charge recovery may be one method of generating a biphasic, charge-balanced pulse as desired for tissue stimulation without severe side effects due to a DC component of the current.

The neurostimulation pulse may by monophasic (anodic or cathodic), biphasic, and/or multi-phasic. In the case of the biphasic or multi-phasic pulse, the pulse may be symmetrical or asymmetrical. Its shape may be rectangular or exponential or a combination of rectangular and exponential waveforms. The pulse width of each phase may range between e.g., about 0.1 µsec. to about 1.0 sec., as non-limiting examples.

Pulses may be applied in continuous or intermittent trains (i.e., the stimulus frequency changes as a function of time). In the case of intermittent pulses, the on/off duty cycle of pulses may be symmetrical or asymmetrical, and the duty cycle may be regular and repeatable from one intermittent burst to the next or the duty cycle of each set of bursts may vary in a random (or pseudo random) fashion. Varying the stimulus frequency and/or duty cycle may assist in warding off habituation because of the stimulus modulation.

The stimulating frequency may range from e.g., about 1 Hz to about 300 Hz. The frequency of stimulation may be constant or varying. In the case of applying stimulation with varying frequencies, the frequencies may vary in a consistent and repeatable pattern or in a random (or pseudo random) fashion or a combination of repeatable and random patterns.

In a representative embodiment, the stimulator may be set to an intensity (e.g., 1-2 mA (or 0.1-40 mA, or 0.01-200 mA), 100-300 us (or 40-1000 us, or 1-10,000 us)) sufficient to activate the targeted nerve at some distance X1 (e.g., 1 mm) away (from the targeted peripheral nerve). If the stimulus intensity is too great, it may generate muscle twitch(es) or contraction(s) sufficient to disrupt correct placement of the lead. If stimulus intensity is too low, the lead may be advanced too close to the targeted peripheral nerve (beyond the optimal position), possibly leading to incorrect guidance, nerve damage, mechanically evoked sensation (e.g., pain and/or paresthesia) and/or muscle contraction (i.e. when the lead touches the peripheral nerve), inability to activate the target nerve fiber(s) without activating non-target nerve fiber(s), improper placement, and/or improper anchoring of the lead (e.g., the lead may be too close to the nerve and no longer able to anchor appropriately in the muscle tissue).

Patient sensation may instead be used to indicate lead location relative to the targeted peripheral nerve as indicator(s) of lead placement (distance from the peripheral nerve to electrode contact). Any combination of stimulus parameters that evoke sensation(s) may be used. The stimulation parameters may include, but are not limited to frequency, pulse duration, amplitude, duty cycle, patterns of stimulus pulses, and waveform shapes. Some stimulus parameters may evoke a more desirable response (e.g., more comfortable sensation, or a sensation that may be correlated with or specific to the specific target nerve fiber(s) within the targeted peripheral nerve. As an example, higher frequencies (e.g., 100 Hz or 12 Hz) may evoke sensation(s) or comfortable paresthesia(s) in the region(s) of pain or in alternate target region(s).

While stimulation is being applied, the lead 12 (non-limiting examples of the lead could include a single or multi-contact electrode that is designed for temporary (percutaneous) or long-term (implant) use or a needle electrode (used for in-office testing only)) may be advanced (e.g., slowly advanced) towards the targeted peripheral nerve until the desired indicator response (e.g., patient sensation, and/or pain relief) is obtained. The intensity may then be decreased (e.g., gradually decreased) as the lead 12 is advanced (e.g., advanced slowly) closer to the targeted nerve until the desired indicator response(s) may be obtained at smaller intensity(ies) within a target range (e.g., 0.1-1.0 mA (or 0.09-39 mA, or 0.009-199 mA), 100-300 us (or 40-1000 us, or 1-10,000 us)).

In the present teachings, the electrode 14 may be placed and anchored at about 1 millimeter to about 100 millimeters spaced from the target nerve, more preferably from about 1 millimeter to about 50 millimeters spaced from the target nerve. The electrode may touch the nerve, however, this is sub-optimal. The electrode spacing from a targeted nerve may depend on various factors, and similar stimulation settings may invoke different responses even if spaced at similar distances. Thus, electrode spacing from the nerve may be about 10 to about 20 millimeters for one target nerve at a given stimulation intensity while the spacing may be about 20 to about 40 millimeters for a second target nerve at the same stimulation intensity.

If specific response(s) (e.g., desired response(s) and/or undesired response(s)) may be obtained at a range of intensities that are too low, then the lead may be located in a non-optimal location (e.g., too close to the target nerve(s)). In such situations, therefore, the clinician may adjust the lead location until the appropriate responses are achieved from the patient.

The stimulus intensities may be a function of many variables. The stimulus intensities set forth herein are meant to serve as non-limiting examples only, and may need to be scaled accordingly. As a non-limiting example, if electrode shape, geometry, or surface area were to change, then the stimulus intensities may need to change appropriately. For example, if the intensities were calculated for a lead with an electrode surface area of approximately 20 $mm^2$, then they may need to be scaled down accordingly to be used with a lead with an electrode surface area of 0.2 $mm^2$ because a decrease in stimulating surface area may increase the current density, increasing the potential to activate excitable tissue (e.g., target and non-target nerve(s) and/or fiber(s)). Alternatively, if the intensities were calculated for a lead with an electrode surface area of approximately 0.2 $mm^2$, then the intensities may need to be scaled up accordingly to be used with a lead with an electrode surface area of 20 $mm^2$. Alternatively, stimulus intensities may need to be scaled to account for variations in electrode shape or geometry (between or among electrodes) to compensate for any resulting variations in current density. In a non-limiting example, the electrode contact surface area may be 0.1-20 $mm^2$, 0.01-40 $mm^2$, or 0.001-200 $mm^2$. In a further non-limiting example, the electrode contact configuration may include one or more of the following characteristics: cylindrical, conical, spherical, hemispherical, circular, triangular, trapezoidal, raised (or elevated), depressed (or recessed), flat, and/or borders and/or contours that are continuous, intermittent (or interrupted), and/or undulating.

Stimulus intensities may need to be scaled to account for biological factors, including but not limited to patient body size, weight, mass, habitus, age, and/or neurological condition(s). As a non-limiting example, patients that are older, have a higher body-mass index (BMI), and/or neuropathy (e.g., due to diabetes) may need to have stimulus intensities scaled higher (or lower) accordingly.

As mentioned above, if the lead is too far away from the targeted peripheral nerve, then stimulation may be unable to evoke the desired response (e.g., comfortable sensation(s) (or paresthesia(s)), and/or pain relief) in the desired region(s) at the desired stimulus intensity(ies). If the lead is too close to the targeted peripheral nerve, then stimulation may be unable to evoke the desired response(s) (e.g., comfortable sensation(s) (or paresthesia(s)), and/or pain relief) in the desired region(s) at the desired stimulus intensity(ies) without evoking undesirable response(s) (e.g., unwanted and/or painful sensation(s) (or paresthesia(s)), increase in pain, and/or generation of additional pain in related or unrelated area(s)). In some cases, it may be difficult to locate the optimal lead placement (or distance from the targeted peripheral nerve) and/or it may be desirable to increase the range stimulus intensities that evoke the desired response(s) without evoking the undesired response(s) so alternative stimulus waveforms and/or combinations of leads and/or electrode contacts may be used. A non-limiting example of alternative stimulus waveforms may include the use of a pre-pulse to increase the excitability of the target fiber(s) and/or decrease the excitability of the non-target fiber(s).

This stimulation may be used pre-operatively or intra-operatively to limit or prevent post-operative pain. Those skilled in the art will recognize that, for simplicity and clarity, the full structure and operation of all devices and processes suitable for use with the present teachings are not being depicted or described herein.

III. Example of a Method of Use

Following a total knee arthroplasty ("TKA"), the majority of patients experience moderate to severe acute pain, and a lesser number continue to experience moderate to severe subacute pain. Acute and subacute postoperative pain may limit early functional recovery, which is critical to full rehabilitation. The patients experience different types of pain, including nociceptive, inflammatory, and neuropathic pain. The knee is innervated by the femoral, lateral femoral cutaneous, obturator, and the sciatic nerves. Anesthetic block of these nerves individually or as a group may reduce acute pain following a TKA. Accordingly, electrical stimulation of nerves that innervate, or portions of which innervate, a portion of the body (specifically a limb or joint) to undergo limb joint replacement surgery, where such stimulation occurs before, during and/or after limb joint replacement surgery may be used to reduce pain and enhance recovery. In this example, if the targeted peripheral nerve includes nerves of the femoral and sciatic nerves and/or their nerve branches, the method may include:

1) Place the patient in a comfortable and/or appropriate position.

2) Ask the patient to shade their area of pain on a diagram of the body. For example, as shown in FIG. 16, the shaded areas indicate where the patient was experiencing pain.

3) Prepare the lead insertion site with antiseptic and local subcutaneous anesthetic (e.g., 2% lidocaine) may be used as well.

4) Locate the site of skin puncture with appropriate landmarks, such as the inguinal crease and femoral artery (for the femoral nerve) and the interior and lateral (ventral) to the midpoint of the line connection greater trochanter and ishical tuberosity (for the sciatic nerve).

5) Insert a sterile percutaneous electrode lead 12 preloaded in the introducer needle 30 at a predetermined angle based on the landmarks used. The lead may be of any appropriate configuration, such as by way of a non-limiting example, a single fine wire with one lead to target each nerve.

6) Place a surface stimulation return electrode in proximity to the lead insertion site. The surface electrode may be placed adjacent to the insertion site. Its position is not critical to the therapy and it may be moved throughout the therapy to reduce the risk of skin irritation, but care should be taken to place the electrode distant from the surgical incision to generally avoid infection.

7) Couple the lead 12 to the external pulse generator 28 and to the return electrode. Set the desired stimulation parameters on the external pulse generator 28, or through a controller. Test stimulation may be delivered using a current-regulated pulse generator, for example. The external pulse generator 28 may be a battery-powered stimulator, for example.

8) Advance the introducer slowly until the subject reports the first evoked sensation in the region experiencing pain. Progressively reduce the stimulus amplitude and advance the introducer more slowly until the sensation can be evoked in the painful region at predetermined stimulus amplitude (e.g., 1 mA). Stop the advancement of the introducer, and increase the stimulus amplitude in small increments (e.g., 0.1 mA) until the stimulation-evoked tingling sensation (paresthesia) expands to overlay the entire region of pain. The electrode may be located at an area to generate maximal paresthesia coverage of the religion of pain, as defined by a patient shaded diagram of the body. During stimulation, the patient is asked to estimate how much of the area of pain is covered by paresthesia. For example, as in FIG. 16, the shaded regions indicate where the patient experiences paresthesia during stimulation.

9) Withdraw the introducer 30, leaving the percutaneous lead 12 in proximity but away from the target nerve. Further, a plurality of leads may be placed percutaneously near or approximately adjacent to the nerves innervating the regions of pain, and stimulation may be applied to determine optimal stimulus parameters and lead locations.

10) Cover the percutaneous exit site and lead 12 with a bandage. A bandage may also be used to secure the external portion of the lead 12 (or an extension cable may be used to couple the lead 12 to the external pulse generator) to the skin. It is expected the length of time to place the lead 12 to be less than 10 minutes, although the process may be shorter or longer.

11) The external pulse generator 28 may be programmed to 100 Hz, 15 µs with amplitude sufficient to generate maximum paresthesia coverage. The parameter may include 100% duty cycle (for both femoral and sciatic) for 24 hours per day. The stimulation may be on for the duration of the acute or subacute pain of the patient. Patients may receive the stimulation therapy for a predetermined time, such as by way of a non-limiting example, two to four weeks.

12) It is possible that stimulation intensity may need to be increased slightly during the process due to causes such as habituation or the subject becoming accustomed to sensation. However the need for increased intensity may be unlikely and usually only occurs after several days to weeks to months as the tissue encapsulates and the subject accommodates to stimulation. It is to be appreciated that the need for increased intensity may happen at any time, which may be due to either lead migration or habituation, but may also be due reasons ranging from nerve damage to plasticity/reorganization in the central nervous system.

13) Prior to insertion of the lead and introducer needle, a sterile test needle may be used to deliver stimulation and determine the desired site of insertion.

14) If paresthesia cannot be evoked with the initial lead placement, redirect the introducer 30.

15) If stimulation fails to elicit paresthesia in a sufficient region (e.g., ≥50%) of pain, then a second percutaneous lead (not shown) may be placed to stimulate the nerves that are not activated by the first lead 12, i.e., the nerves innervating the region of post-operative pain.

Percutaneous electrical stimulation of nerves innervating the knee as discussed in the example above may be used to generate paresthesia to provide pain relief for any type of post-op pain following a limb joint replacement surgery (e.g., immediate acute phase=0 to 3-5 days; post acute or subacute phase=3-5 days to 30 days). In this approach, one might use the femoral and sciatic nerves, or they may also stimulate the lumbar plexus to target the femoral, obturator, and/or lateral femoral cutaneous nerves. Additionally, there may be an anterior approach as well as a posterior approach to targeting these nerves.

An alternative embodiment may include using a needle electrode/lead and placing it during insertion of needles used during anesthetic peripheral nerve block. Additionally, in a different embodiment the pulse trains may be varied, as varied pulse shapes may improve selectivity of activation of paresthesia-fibers versus pain fibers. Percutaneous electrical stimulation of nerves may provide some pain relief as anesthetic block without many of its drawbacks. This therapy may be provided as a temporary therapy or as a permanent implant. Acute pain relief may allow patients to recover sufficiently enabling them to begin rehabilitation, which is critical to regaining normal function and natural pain relief. It is generally thought that if 50% paresthesia coverage is achieved, then there is a 70% success rate. Oftentimes after the stimulation therapy, the pain will never return to the patient.

Although TKA is discussed herein, it is to be understood that the systems and methods may be employed to condition a body before or after any limb joint replacement surgery. While stimulation of the femoral and/or sciatic nerves should generally provide relief of pain following a limb joint replacement surgery of the leg, more distal peripheral nerves may be targets for surgeries related to distal portions of the leg (foot, ankle surgery, e.g.). For arm/hand limb joint replacement surgery-related pain, nerves near the brachial plexus, near or below the shoulder, elbow, or wrist may be targeted.

In peripheral nerve stimulation, the lead may be placed in a tissue by which the targeted nerve passes, but stimulation actually relieves pain that is felt distal (downstream) from where the lead is placed. In peripheral nerve stimulation, the lead may be placed in a tissue that is conveniently located near a nerve trunk that passes by the lead on the way to or from the painful area. The key is that the lead may be placed in a tissue that is not the target (painful) tissue, but rather a tissue that is located away from the painful region, which is a safer and more convenient location to place the lead.

Peripheral nerve stimulation may be easily used by clinicians, including, but to limited to, general surgeons, orthopedic surgeons, and anesthesiologists, who are used to placing needles deeper in the tissue near peripheral nerves. For example, anesthesiologists are accustomed to placing needles distant from the areas of pain to numb the areas of pain. Anesthesiologists often already use ultrasound and the electro-location techniques that may be needed to place leads to access peripheral nerves. This may result in the system and method to be used in practice with little or no training.

Peripheral nerve stimulation may provide stimulation-generated paresthesia (that ideally overlap with the area of pain) but may not require evoking a muscle contraction to place the lead correctly. The target regions in which pain is felt and which are targeted for generation of paresthesia may not be the same region in which the lead is placed. This may be useful because physicians (e.g., anesthesiologists) who will typically be placing the lead are accustomed to using paresthesia (sensory feedback description of from the patient) to guide lead placement and tuning of stimulation parameters.

Imaging (e.g., ultrasound or an alternate imaging technique, e.g., fluoroscopy) may be used to improve lead placement near peripheral nerves. Ultrasound may improve lead placement in the form of increasing the total speed of the procedure. Specifically, ultrasound may shorten the procedure's duration by locating the lead in a more optimal location. Doing so may: improve recruitment of the target fibers in the target nerve and minimize recruitment of non-target fibers in either the target nerve and/or in non-target nerve(s); and minimize risk and/or damage to the patient during placement of the lead by avoiding blood vessels, organs, bones, ligaments, tendons, lymphatic vessels, &/or other structures that may be damaged. One reason that imaging may be useful is that some peripheral nerves are (but do not have to be) located relatively deeply. Alternatively, fluoroscopy may be desirably avoided, thus lessening the cost of the procedure and the risk of radiation exposure.

In the present system and method, the patient may not need to give verbal, written, or other type of feedback or indication of what they feel as the lead is being advanced towards the peripheral nerve if imaging is used to guide lead placement. In addition, any known method for non-verbal communication can be used, including those used by anesthesiologists. This allows for the system to be placed in an unconscious patient, e.g., in a sedated patient or intra-operatively. However, patient feedback during lead advancement may improve lead placement in some patients. The patient may indicate sensations during tuning of stimulus intensity. As non-limiting examples, those sensations reported by the patient may include first sensation (minimum stimulus intensity that evokes a sensation), level of comfort, maximum tolerable sensation, pain, qualities or descriptions of the sensations.

Alternatively, if the system is used preoperatively, as there will not be any patient feedback of post-operative pain to guide the paresthesia coverage, the optimal coverage would be a region that is likely to be painful following the limb joint replacement surgery (e.g., in the case of a TKA, both the front and back of the knee).

The region in which the patient perceives stimulation-induced sensations or paresthesia may be an important indicator of the potential success of the therapy. This may help screen potential candidates and may help determine the appropriate stimulation parameters (including but not limited to lead location). Further, such parameters may be adjusted so that the region in which paresthesia is perceived overlaps with the region of pain.

As an alternative to using perception of stimulation induced sensations and/or paresthesia, the level of pain or change in the intensity of pain during or due to stimulation may be used to adjust stimulation parameters (including but not limited to lead location). For example, if a patient is experiencing "very high" pain before stimulation, no sensory or motor responses are evoked and during stimulation, if the pain decreases to "low", the system would be considered satisfactory in the patient.

Although the embodiments of the present invention have been illustrated in the accompanying drawings and described in the foregoing detailed description, it is to be understood that the present invention is not to be limited to just the embodiments disclosed, but that the invention described herein is capable of numerous rearrangements, modifications and substitutions without departing from the scope of the claims hereafter. The claims as follows are intended to include all modifications and alterations insofar as they come within the scope of the claims or the equivalent thereof

The invention claimed is:

1. A method to alleviate pain following a limb joint replacement surgery, the method comprising the steps of:
   inserting at least one electrode within a therapeutically effective distance from at least one nerve, wherein the at least one electrode is outside of a region of expected pain from the limb joint replacement surgery;
   applying electrical stimulation through the at least one electrode to affect the at least one nerve innervating the region of expected pain from the limb joint replacement surgery in advance of the limb joint replacement surgery;
   causing an area of paresthesia;
   comparing the area of paresthesia caused by the electrical stimulation with the region of expected pain from the joint replacement surgery; and
   applying electrical stimulation through the at least one electrode after the limb joint replacement surgery.

2. The method of claim 1, further comprising the steps of:
   repositioning the at least one electrode within the therapeutically effective distance from the at least one nerve;
   applying electrical stimulation through the repositioned at least one electrode to affect the at least one nerve innervating a region of pain following the limb joint replacement surgery; and
   comparing an area of paresthesia caused by the electrical stimulation with the region of pain following the limb joint replacement surgery.

3. The method of claim 1, wherein applying electrical stimulation through the at least one electrode after the limb joint replacement surgery includes a first set of electrical stimulation parameters.

4. The method of claim 3, wherein the first set of electrical stimulation parameters is selected from a group consisting of:

frequency, pulse duration, amplitude, duty cycle, pattern of stimulus pulses, polarity, a predetermined number of phases, and wave form shape.

5. The method of claim 3, further comprising the steps of:
comparing an area of paresthesia caused by the electrical stimulation with a region of pain following the limb joint replacement surgery;
applying electrical stimulation through the at least one electrode after the limb joint replacement surgery, wherein the electrical stimulation includes a set of second electrical stimulation parameters; and
comparing an area of paresthesia caused by the electrical stimulation with the region of pain following the limb joint replacement surgery.

6. The method of claim 1, wherein causing the area paresthesia occurs without damaging the at least one nerve.

7. The method of claim 6, wherein the at least one nerve is a peripheral nerve.

8. The method of claim 1, wherein the limb joint replacement surgery is selected from a group consisting of: a shoulder, elbow, wrist, finger joint, hip, knee, ankle and toe joint.

9. The method of claim 1, further comprising the steps of:
evaluating pain relief associated with the electrical stimulation after the limb joint replacement surgery.

10. The method of claim 9, further comprising the steps of:
applying a second set of stimulation parameters; and
evaluating pain relief associated with the second set of stimulation Parameters of the electrical stimulation.

11. The method of claim 10, wherein the second set of electrical stimulation parameters is selected from a group consisting of:
frequency, pulse duration, amplitude, duty cycle, pattern of stimulus pulses, polarity, a predetermined number of phases, and wave form shape.

12. The method of claim 1, wherein the at least one nerve is selected from a group consisting of a femoral nerve, a sciatic nerve, lateral femoral cutaneous nerve, and an obturator nerve.

13. A method to alleviate pain post limb joint replacement surgery, the method comprising:
identifying a tissue region innervated by a peripheral nerve innervating an expected targeted region of pain resulting from the limb joint replacement surgery;
placing at least one electrode within the tissue region near the peripheral nerve outside of the expected targeted region of pain;
applying electrical stimulation through the at least one electrode to activate the peripheral nerve;
evoking a tingling sensation in the expected targeted region of pain without functional nerve stimulation at a motor point and without damaging the peripheral nerve in advance of the limb joint replacement surgery;
applying electrical stimulation through the at least one electrode after the limb joint replacement surgery;
evoking a second tingling sensation in an area of paresthesia; and
comparing the area of paresthesia caused by the electrical stimulation with a region of pain occurring after the limb joint replacement surgery.

14. The method of claim 13, further comprising the steps of:
re-placing the at least one electrode within the tissue region near the peripheral nerve outside of the expected targeted region of pain;
re-applying electrical stimulation through the at least one electrode;
causing a second area of paresthesia; and
re-comparing the second area of paresthesia caused by the electrical stimulation with the region of pain resulting from the limb joint replacement surgery.

15. The method of claim 13, wherein applying electrical stimulation through the at least one electrode after the limb joint replacement surgery includes a first set of electrical stimulation parameters.

16. The method of claim 15, further comprising the steps of:
applying electrical stimulation through the at least one electrode after the limb joint replacement surgery, wherein the reapplied electrical stimulation includes a set of second electrical stimulation parameters, wherein at least one of the second electrical stimulation parameters is different from at least one of the first electrical stimulation parameters; and
comparing an area of paresthesia caused by the electrical stimulation with the region of pain.

17. The method of claim 16, wherein the at least one of the second electrical stimulation parameters includes at least one of frequency, pulse duration, amplitude, duty cycle, pattern of stimulus pulses, polarity, a predetermined number of phases, and wave form shape.

18. The method of claim 13, wherein the limb joint replacement surgery includes total knee arthroplasty.

19. The method of claim 18, wherein the peripheral nerve includes the femoral nerve.

20. The method of claim 13, wherein the electrode is located in tissue that is distal from the region of pain.

* * * * *